(12) United States Patent
Witchey et al.

(10) Patent No.: US 12,626,791 B2
(45) Date of Patent: May 12, 2026

(54) SAMPLE TRACKING VIA SAMPLE TRACKING CHAINS, SYSTEMS AND METHODS

(71) Applicant: Nant Holdings IP, LLC, Culver City, CA (US)

(72) Inventors: Nicholas James Witchey, Laguna Hills, CA (US); Patrick Soon-Shiong, Los Angeles, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 18/620,779

(22) Filed: Mar. 28, 2024

(65) Prior Publication Data

US 2024/0242795 A1      Jul. 18, 2024

Related U.S. Application Data

(63) Continuation of application No. 17/171,584, filed on Feb. 9, 2021, now Pat. No. 11,990,211, which is a
(Continued)

(51) Int. Cl.
*G06F 19/00* (2018.01)
*G06Q 10/0633* (2023.01)
(Continued)

(52) U.S. Cl.
CPC ......... *G16H 10/40* (2018.01); *G06Q 10/0633* (2013.01); *G16H 10/60* (2018.01); *G06F 16/90335* (2019.01)

(58) Field of Classification Search
CPC .... G16H 10/40; G16H 10/60; G06Q 10/0633; G06F 16/90335
See application file for complete search history.

(56) References Cited

U.S. PATENT DOCUMENTS

| | | |
|---|---|---|
| 10,923,215 B2 | 2/2021 | Witchey et al. |
| 2007/0124084 A1 | 5/2007 | Torre-Bueno |

(Continued)

FOREIGN PATENT DOCUMENTS

| | | |
|---|---|---|
| JP | 2000276545 A | 10/2000 |
| JP | 2016122917 A | 7/2016 |
| WO | 2016097166 A1 | 6/2016 |

OTHER PUBLICATIONS

Office Action from corresponding Canadian Application No. 3,037,674 dated Apr. 29, 2020.

(Continued)

*Primary Examiner* — Maroun P Kanaan
(74) *Attorney, Agent, or Firm* — Harness Dickey & Pierce P.L.C.

(57) ABSTRACT

Systems and methods for tracking samples via sample tracking chains are presented. Sample tracking chains represent digital data structures instantiated according to intrinsic properties of a sample. Each link in the chain is a block of data representing an observed intrinsic state of the sample and is linked at least to a previous block representing a previous state. The sample tracking chain and blocks can be indexed for later retrieval by the intrinsic properties of the corresponding sample's state. The sample tracking chain can take the form of a blockchain possibly stored as part of a private or public distributed ledger. Disclosed sample tracking chains provide a full life cycle audit trail for sample processing.

19 Claims, 5 Drawing Sheets

Related U.S. Application Data continuation of application No. 15/708,837, filed on Sep. 19, 2017, now Pat. No. 10,923,215.

(60) Provisional application No. 62/396,986, filed on Sep. 20, 2016.

(51) Int. Cl.

| | | |
|---|---|---|
| *G16H 10/40* | (2018.01) | |
| *G16H 10/60* | (2018.01) | |
| *G06F 16/903* | (2019.01) | |

(56) References Cited

U.S. PATENT DOCUMENTS

| | | | |
|---|---|---|---|
| 2008/0040151 A1 | 2/2008 | Moore | |
| 2008/0235055 A1 | 9/2008 | Mattingly et al. | |
| 2010/0167334 A1 | 7/2010 | Williamson, IV | |
| 2010/0198620 A1 | 8/2010 | Mullenger et al. | |
| 2014/0297325 A1 | 10/2014 | Kasprisin et al. | |
| 2015/0039342 A1 | 2/2015 | Chen et al. | |
| 2015/0332283 A1 | 11/2015 | Witchey | |
| 2016/0084862 A1 | 3/2016 | Feingold et al. | |
| 2017/0089689 A1 * | 3/2017 | Boyle | G06T 7/30 |
| 2019/0331702 A1 * | 10/2019 | Menhardt | G06Q 10/0833 |
| 2021/0166792 A1 | 6/2021 | Witchey et al. | |

OTHER PUBLICATIONS

Office Action from corresponding Japanese Application No. 2019-537025 dated Oct. 19, 2021.

Azaria, A., et al., "MedRec: Using Blockchain for Medical Data Access and Permission Management," 2nd International Conference on Openand Big Data, p. 25-30 (2016).

International Search Report from corresponding PCT Application No. PCT/US2017/052284 dated Nov. 22, 2017.

Written Opinion from corresponding PCT Application No. PCT/US2017/052284 dated Nov. 22, 2017.

International Preliminary Report on Patentability from corresponding PCT Application No. PCT/US2017/052284 dated Mar. 26, 2019.

Office Action from U.S. Appl. No. 17/171,584 dated Sep. 28, 2023.

* cited by examiner

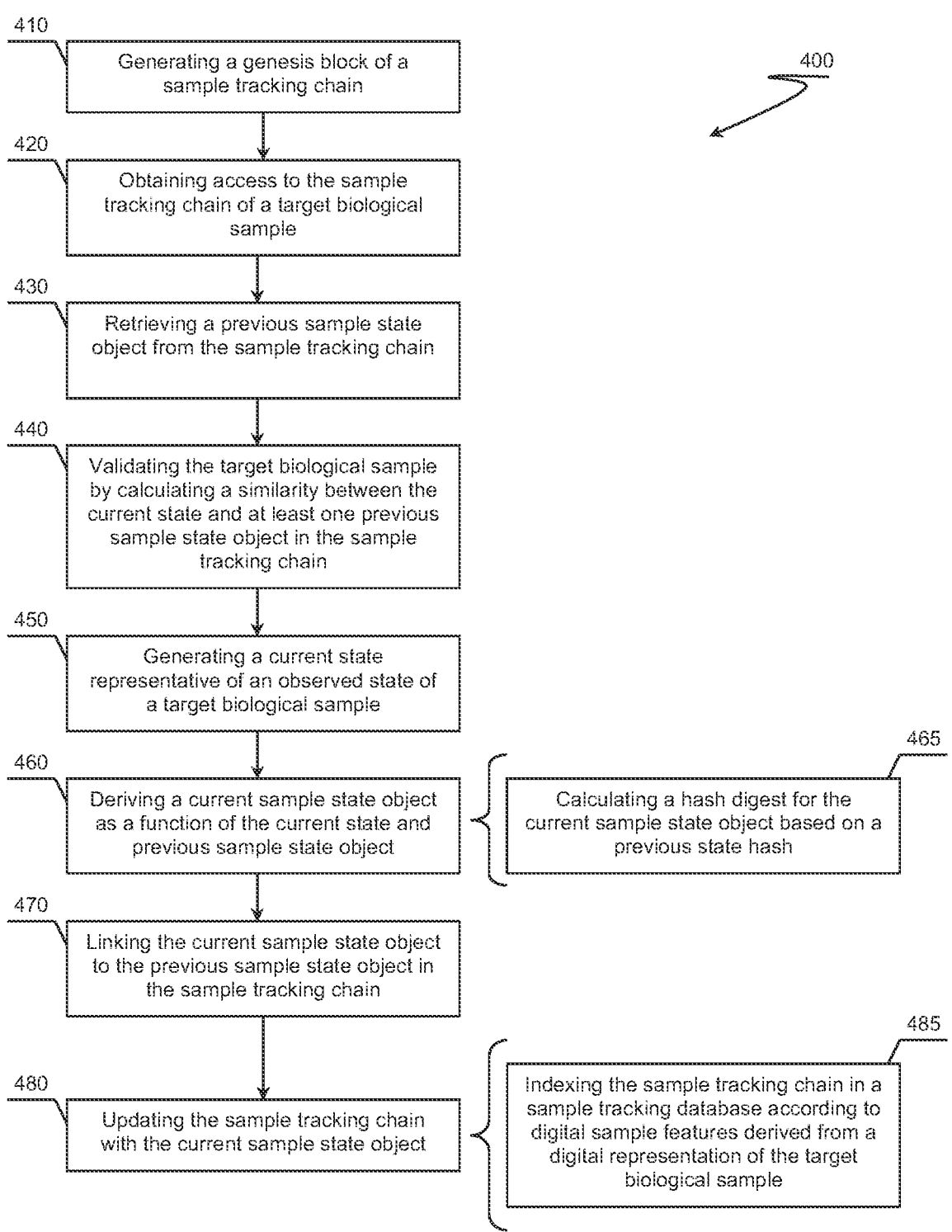

410

Generating a genesis block of a sample tracking chain

420

Obtaining access to the sample tracking chain of a target biological sample

430

Retrieving a previous sample state object from the sample tracking chain

440

Validating the target biological sample by calculating a similarity between the current state and at least one previous sample state object in the sample tracking chain

450

Generating a current state representative of an observed state of a target biological sample

460

Deriving a current sample state object as a function of the current state and previous sample state object

465

Calculating a hash digest for the current sample state object based on a previous state hash

470

Linking the current sample state object to the previous sample state object in the sample tracking chain

480

Updating the sample tracking chain with the current sample state object

485

Indexing the sample tracking chain in a sample tracking database according to digital sample features derived from a digital representation of the target biological sample

Tumor Markup

Post Laser
Microdissection

SAMPLE TRACKING VIA SAMPLE TRACKING CHAINS, SYSTEMS AND METHODS

CROSS-REFERENCE TO RELATED APPLICATIONS

This application is a continuation of U.S. application Ser. No. 17/171,584, filed on 9 Feb. 2021, which is a continuation of U.S. application Ser. No. 15/708,837, filed on 19 Sep. 2017, which claims priority to U.S. Provisional Application No. 62/396,986, filed on 20 Sep. 2016. The contents of each application recited above are incorporated by reference herein in their entirety.

FIELD OF THE INVENTION

The field of the invention is digital state tracking technologies.

BACKGROUND

The background description includes information that may be useful in understanding the systems and methods described herein. It is not an admission that any of the information provided herein is prior art, or that any publication specifically or implicitly referenced is prior art.

Many medical treatments, especially oncological treatments require analysis of one or more biological samples taken from a patient. Typically such samples are extrinsically labeled for tracking or identification purposes. For example, a sample in a container might have a bar code or patient identifier label affixed to its container As the samples are processed through a workflow, a technician can scan such labels to ensure the sample properly works its way through the analysis workflow or its complete life cycle. Unfortunately, even in today's computer driven environments, biological sample tracking is fraught with issues; many of which arise due to the nature of the computing environments. One issue is that labels are generated extrinsically, which creates an opportunity for a worker to place a wrong label on the sample either accidently or due to improper data entry. Another issue is that the data generated through the analysis is merely stored in a database only accessible via the extrinsic information (e.g., bar code, label, patient's name, etc.) without having a built-in mechanism to validate that the retrieved data is, in fact, associated with the target biological sample.

Consider the following efforts applied to tracking biological samples. U.S. Pat. No. 8,431,078 to Schutze et al. titled "Sample Holder for a Reception Device Receiving Biological Objects and Microscope System Designed to Operate Using One Such Sample Holder", filed internationally Nov. 20, 2003, describes a system that attempts to ensure unambiguous identification of samples by a microdissection device. The Schutze system requires that a sample holder have a coding that can be used to present selection functions to a user on a display. While useful for controlling a microdissection device in a manner appropriate for a sample, the disclosed system fails to provide insight into tracking biological samples through an entire life cycle of analysis and into creation of an intrinsic audit trail. Further, if the coding of the sample holder is mislabeled, then incorrect functions could be presented to a technician.

Further progress is made by U.S. Pat. No. 8,676,509 to De La Torre-Bueno titled "System for Tracking Biological Samples" filed Nov. 13, 2002. De La Torre-Bueno seeks to provide real-time tracking of samples from collection through to storage. Samples are associated with unique bar code identifiers that link to processing steps at various workstations. Such an approach aids in reducing possible processing errors with respect to managing slides. However, the system still requires significant interaction on the part of humans to tag the samples in the first place. Again, if at any time the bar code is incorrectly used, the slides could be mismanaged. Still further, the bar code tags could degrade over time reducing their efficacy for use over long term studies.

Yet another example includes U.S. Pat. No. 9,354,147 to Lefebvre "Automated System and Method of Processing Biological Specimens" filed May 28, 2014. Lefebvre focuses on an automated system that transports specimen slides to and from an imaging unit. In addition, Lefebvre indicates that the slides, as well as other items in the system, can be identified with machine understandable codes (e.g., RFID, barcodes, etc.). Again, such systems are considered useful as tracking system elements. However, such tags or codes can be damaged over time rendering them less useful or the codes; and yet again, could be mishandled.

Still further effort has been directed to binding patient information with sample identifier information at a high level. For example, U.S. patent application publication U.S. 2008/0235055 to Mattingly et al. titled "Laboratory Instrumentation Information Management and Control Network", filed Jun. 13, 2007, discusses forming a harmonized specimen identifier from a case identifier of a patient and a specimen identifier. The harmonized specimen identifier represents a combination of identifiers arranged in a defined format, possibly a hierarchal format, where the various identifiers aid in tracking a specimen at different points in a workflow. However, Mattingly's harmonized specimen identifiers also fail to provide robustness over time and lack specific intrinsic bindings to the content of the specimen. Thus, the Mattingly approach still relies only on extrinsic information outside of the sample.

Interestingly, there has also been additional effort toward digitally processing biological samples via pattern recognition algorithms. For example, U.S. patent application publication 2015/0003716 to Lloyd et al. titled "Histology Recognition to Automatically Score and Quantify Cancer Grades and Individual User Digital Whole Histological Image Device" filed internationally on Jan. 18, 2013, discusses conducting cancer cell classification based on features of imaged cells. Unfortunately, Lloyd also fails to provide insight into how to bind specimen or slide content to create a robust tracking system.

In a somewhat similar vein, international patent application publication WO 02/48680 to Kallioniemi et al. titled "Method and System for Processing Regions of Interest for Objects Comprising Biological Material" also uses patterns to process biological samples. Kallioniemi describes using reference points within a biological sample to find regions of interest. Kallioniemi also lacks any insight into a robust tracking system capable of tracking samples through a full analysis lifecycle or binding slide content to tracking information.

Traditional techniques of implementing blockchain technology can be computationally intensive, leading to significant latency and relying on specialized hardware for computation. In order to address such issues, technologies such as Microsoft's Confidential Consortium (CoCo) are in development, with the aim of making blockchain-based systems faster and providing improvements over privacy of data.

Enterprise blockchain approaches include openchain (www.openchain.org) and Ethereum, which are open source distributed ledger technology platforms. Enterprise blockchain solutions are geared towards management of digital data in a robust, scalable, and secure way with capabilities extending beyond management of cryptocurrency.

Other approaches, designed to operate in a trusted execution environment include Intel's Sawtooth Lake (see URL intelledger.github.io/0.7/introduction.html). Sawtooth Lake, a distributed ledger platform, implements data models and transaction language using one or more transaction families. Unlike other blockchain approaches, specialized hardware is not needed, and simulations suggest that this approach can scale to thousands of clients.

In a more ideal setting, biological samples would be tracked via more reliable techniques than merely tagging samples with extrinsic codes. Thus there remains a need for new systems or methods through which biological samples can be tracked through an entire analysis life cycle based on the intrinsic features of the biological sample rather than relying solely on extrinsic codes or information.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the subject matter described herein are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the subject matter described herein are approximations, the numerical values set forth in the specific examples are reported as precisely as practicable. The numerical values presented in some embodiments of the subject matter described herein may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the subject matter described herein and does not pose a limitation on the scope of the subject matter described herein otherwise claimed. No language in the specification should be construed as indicating any non-claimed element essential to the practice of the subject matter described herein.

Groupings of alternative elements or embodiments of the subject matter described herein disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY

The subject matter described herein provides apparatus, systems, computer readable media, or methods in which biological samples can be electronically tracked through a workflow based on observed intrinsic properties of the biological sample by generating a digital chain of sample states (e.g., a blockchain, etc.). One aspect of the subject matter described herein includes a biological sample tracking system that includes a sample database, a sample tracking engine, and possibly a sample search engine. The sample database is a computing device configured to store sample tracking chains (i.e., a chain of biological sample states throughout a life cycle of the sample) on a non-transitory, computer readable memory. The sample tracking chain, in typical embodiments, includes a linked chain of state digital objects, possibly forming a single audit trail, where each state object is instantiated to represent a target biological sample at a point in time of its life cycle. The sample tracking engine is also implemented using a computing device (e.g., a server, a workstation, a cell phone, a cloud device, etc.) coupled with the sample database possibly via a computer network or via an internal communication bus. The sample tracking engine comprises at least one processor and computer readable, non-transitory memory storing software instructions. Upon execution of the software instructions by the processor, the sample tracking engine is configurable to process one or more observed states of a target biological sample. The sample tracking engine obtains access to at least one sample tracking chain in the sample database where the sample tracking chain relates to the target biological sample. The sample tracking engine further retrieves at least one previous sample state object, a block data from a previous sample state for example, from the sample tracking chain. The sample tracking engine continues by generating a current state representative of an observed state including intrinsic properties or features of the target biological sample; including, e.g., one or more of a whole slide image, a microdissected image of the sample, density measurements, or other digital data. Using the previous tracking state object and the current state, the sample tracking engine instantiates or otherwise derives a current sample state object; a new block of data. The sample tracking engine also links the current sample state object to the previous sample state object in the sample tracking chain. For example, the previous sample state object can include a hash digest of the data associated with the previous sample state. The previous hash digest can be concatenated with the data from the current state to generate a current hash digest, thus the current hash digest is dependent on the previous hash digest thereby linking the current sample state object to the previous sample state object via their hash values. In some embodiments, the sample tracking chain comprises a blockchain that can be considered a sample-specific audit trail. The sample tracking engine also is able to update the sample tracking chain in the sample database so that the sample tracking chain includes the current sample state object.

In other aspects, hash digests may be generated using static data, including social security number, date of birth, external notary data, or other identifying information that is not variable as a function of time. In some aspects, the hash digest from the static data may be stored for comparison to a subsequent hash of the same static data. This can advantageously provide an additional verification that the static data has not been corrupted or modified. In cases in which the genesis block consists of static data, this can provide validation of the entire genesis block.

Various objects, features, aspects and advantages of the subject matter described herein will become more apparent from the following detailed description of preferred embodiments, along with the accompanying drawing figures in which like numerals represent like components.

BRIEF DESCRIPTION OF THE DRAWING

FIG. 4 represents a method of tracking biological samples via creating or otherwise managing sample tracking chains, according to an embodiment of the techniques disclosed herein.

DETAILED DESCRIPTION

Figure 1:
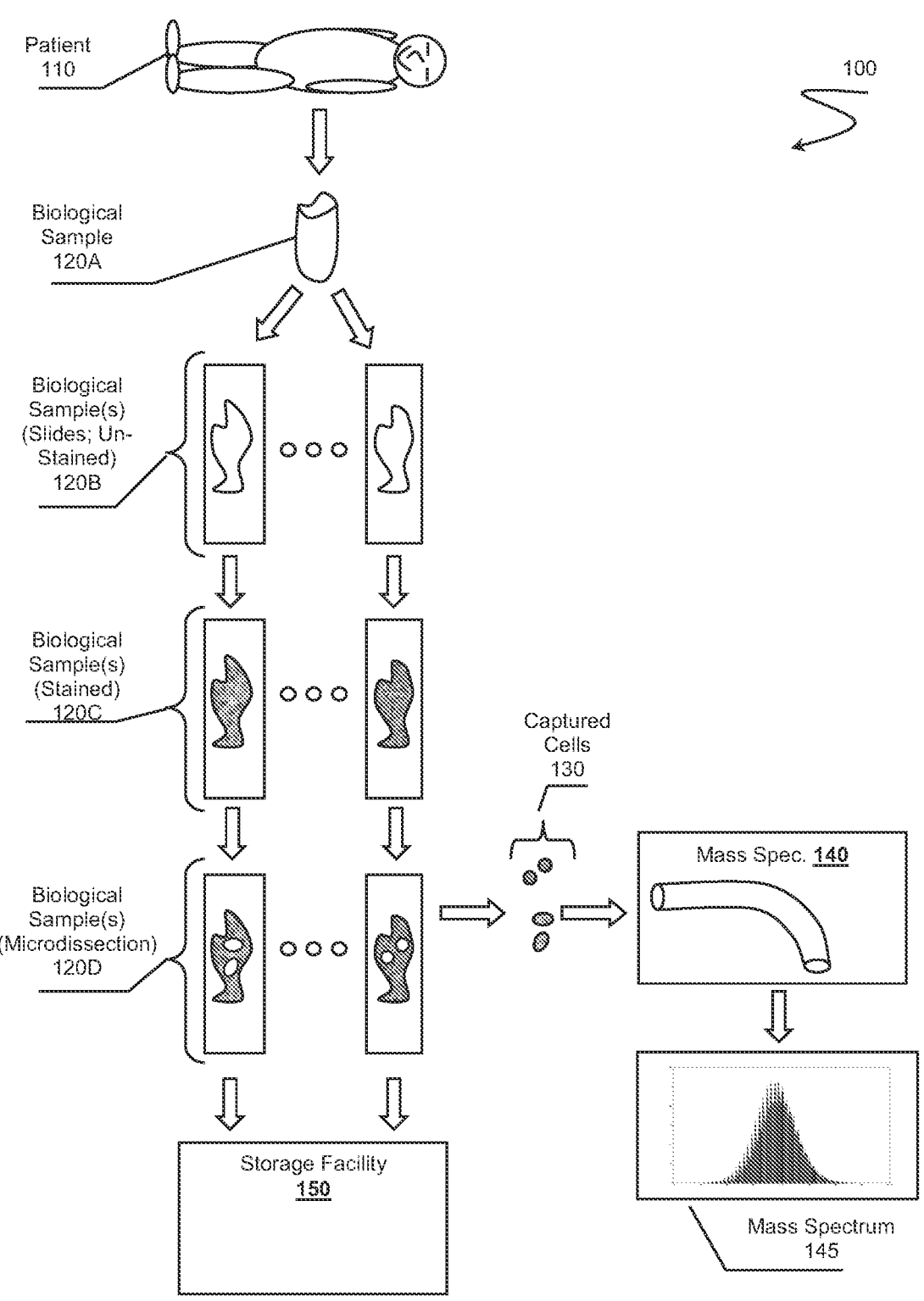
FIG. 1 is an overview of a biological sample life cycle, according to an embodiment of the techniques disclosed herein.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise at least one processor configured to execute a computer program product comprising software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, TCP/IP, UPD/IP, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory. It is understood that the use of "configured to" or "programmed to" (or similar language) should not be construed to invoke interpretation under 35 USC 112(f).

One should appreciate that the disclosed techniques provide many advantageous technical effects including providing low latency access to biological sample data while also providing techniques for validating data in a sample tracking change relative to a physical sample. Accordingly, the present techniques provide a way in which to greatly improve the validity of data, and in particular, data corresponding to an object that may change in appearance as a function of time. Other advantages include predictive capabilities, e.g., such as the ability to predict one or more characteristics of a sample after a processing step has occurred. Still other advantages of the techniques presented herein include the ability to backtrack through the sample tracking chain to previous states, e.g., from T3 to T2, from T2 to T1, from T1 to T0, in order to reconstruct what a sample looked like at a previous state. Through the use of a sample tracking chain data structure stored in memory, intrinsic information about a sample (e.g., size, shape, texture, features, etc.) can be used as an index to access directly sample information without requiring extrinsic information (e.g., bar codes, RFID, etc.). Further, the intrinsic features of the sample can be used to validate that the current state of a sample is in fact a valid state of the sample relative to a previous state of the same sample.

The focus of the disclosed subject matter described herein is to enable construction or configuration of a computing device to operate on vast quantities of digital data in the form of biological sample data, beyond the capabilities of a human. Although the digital data represents biological samples or sample states, it should be appreciated that the digital data is a representation of one or more digital models of an observed sample, not the sample itself. By instantiation of such digital models from intrinsic features of the sample in the memory of the computing device(s), in this case sample tracking chains, the computing device(s) are able to manage the digital data or models in a manner that provide utility to a user of the computing device that the user would lack without such a tool.

The following discussion provides many example embodiments of the subject matter described herein. Although each embodiment represents a single combination of inventive elements, the subject matter described herein is considered to include all possible combinations of the disclosed elements. Thus if one embodiment comprises elements A, B, and C, and a second embodiment comprises elements B and D, then the subject matter described herein is also considered to include other remaining combinations of A, B, C, or D, even if not explicitly disclosed.

As used herein, and unless the context dictates otherwise, the term "coupled to" is intended to include both direct coupling (in which two elements that are informationally coupled to each other contact each other) and indirect coupling (in which at least one additional element is located between the two elements). Therefore, the terms "coupled to" and "coupled with" are used synonymously.

FIG. 1 presents example sample workflow environment 100 in which the subject matter described herein is employed. Environment 100 is presented from the perspective of biological sample 120A (e.g., tumor sample, normal tissue, etc.) flowing through an analysis workflow with the goal of creating one or more microdissected samples for biological analysis (e.g., mass spectrometry, whole genome sequencing, whole exome sequencing, RNA-seq, etc.). Biological sample 120A represents a tissue sample extracted from patient 110; a tumor tissue for example. Although the following discussion presents the subject matter described herein from the perspective that biological sample 120A is a tumor tissue sample, it should be appreciated that the disclosed techniques can be adapted to other types of biological samples including saliva, urine, blood, feces, skin, hair, or other specimens obtained from patient 110. Further, patient 110 is presented as a human. However, patient 110 can also be other forms of mammals or even other animals in general. Thus, the disclosed techniques are of value in other markets beyond human healthcare including veterinary science, animal husbandry, environmental studies, soil samples, gem cutting, tracking machine part production, art restoration, geological studies, clinical trials, long term longitudinal studies, or other areas where rigor is required to track samples or specimens over time. For example, the disclosed techniques can be used to create a blockchain-based audit trail.

Biological sample 120A can be obtained from patient 110 using known techniques or those yet to be invented. Typically biological sample 120A will be tagged or coded in some way (e.g., bar codes, Quick Response (QR) codes, Radio Frequency Identification (RFID), etc.) leveraging extrinsic information. For example, biological sample 120A can be placed into a bio-safe container, to which a QR code is affixed. The QR code can be coded with patient-specific information possibly including a patient name, a patient identifier, a time stamp, or other extrinsic information. More interestingly, the nature of biological sample 120A, or rather intrinsic properties or features of biological sample 120A, can also be used to identify and track the sample. For example, one or more of the following intrinsic properties of the sample can be encoded into the label for the specimen: size, shape, color, mass, weight, density, length, width, volume, tissue type, cell lines, genome sequences, location at which the sample was obtained, date at which the sample was obtained, appearance of container into which the sample is placed, appearance of sample, or other intrinsic information about the specimen or specimens. As discussed below, the intrinsic information, especially sample state information, can be used to index information about biological sample 120A within a sample database.

Continuing with the example in FIG. 1, consider a next stage in the workflow where biological sample 120A is transformed to a new state taking the form of multiple tissue slices disposed on one or more slides as represented by biological samples 120B. To be clear, it should be appreciated that at this stage of the example, it is possible that the original specimen has been transformed into multiple, distinct specimens placed on slides, but not yet stained as indicated. After such a transformation, each of biological samples 120B will have their own intrinsic properties or could have shared, similar intrinsic properties. For example, each slice on the slide will have its own unique specific intrinsic shape or texture while the slices overall might have a similar overall shape especially if the slides are neighboring slices from the specimen. One or more of these intrinsic properties can be quantified digitally to create digital signatures (i.e., intrinsic features) that are leveraged to identify or track the specimens individually or collectively. These newly created digital signatures can also be used to index information about the biological sample 120B as well as being digital representations of the specimens' current state. More specifically, the digital signatures could include shape descriptors (e.g., circularity, edges, etc.), image descriptors (e.g., SIFT, DAISY, etc.), or other types of digital features of the sample. These digital features are also referred to as intrinsic features or properties. Further, as discussed in more detail below with respect to FIG. 2, the digital signatures, along with other desirable information, can be linked to previous state information thereby forming a chain of sample states.

A next stage in workflow 100 includes yet another transformation of the specimens where each tissue slice is stained using one or more stains thereby forming biological samples 120C. It should be appreciated that in this specific example the physical specimens are the same specimens from biological samples 120B. However, biological samples 120C represent a new state of the physical specimens. It is possible that individual stained slides might be stained differently in order to highlight different or various structures of the sample. For example, one slide might be stained with toluidine blue to highlight cell structures, hematoxylin could be used to identify nucleic acids, Wright's stain could be used to identify blood cells, or other types of stains could be used. At this stage there are numerous possible intrinsic properties that can be derived from the observed state of the biological samples 120C. Examples of intrinsic priorities include cell clustering, nucleus density or count, color channel descriptors (e.g., red green blue (RGB), hue saturation value (HSV), wavelengths, etc.) that can depend on staining, shapes, cell boundaries, tissue boundaries, or other types of intrinsic properties that can be more pronounced upon staining. Again, just as discussed above, digital features representing the intrinsic properties can be used to index sample information as well as identify this particular state. In addition, also as discussed above, information about the observed state and the digital features can be linked to the previous state information of biological samples 120B.

In some embodiments, biological samples 120C can be examined by one or more technical experts to identify regions of interest within biological samples 120C. For example where biological samples 120C represent tumor tissue samples placed on slides, a pathologist might review each slide to tag cells as cancerous. The pathologist can identify boundaries around regions of interest, microdissection masks, or other points of interest.

The next stage illustrated in workflow 100 includes biological samples 120D, which represents microdissected versions of biological samples 120C, possibly via laser capture microdissection (LCM; see U.S. Pat. No. 7,381,440 to Ringeisen et al. titled "Biological Laser Printer for Tissue Microdissection via Indirect Photon-Biomaterial Interaction", filed on Jun. 4, 2004). At this stage, example workflow 100 as shown splits into at least two parallel paths. In one path, captured cells 130 obtained from the microdissection process are sent for further analysis. For example, captured cells 130 can be processed for whole genome sequencing, RNA sequencing, proteomics analysis, whole exome sequencing, or other types of analysis. In some embodiments, the microdissected calls are processed via Liquid Tissue® SRM Assays such as those offered by Expression Pathology (see URL www.expressionpathology.com) or as described in U.S. Pat. No. 7,473,532 to Darfler et al. titled "Liquid Tissue Preparation from Histopathologically Processed Biological Samples, Tissues and Cells", filed on Mar. 10, 2004.

In some aspects, a director slide may be prepared as a template for guiding laser dissection in other slides, e.g., thick slice microdissection slides. A director slide may be prepared based on techniques known in the art (see, e.g., URL www.expressionpathology.com/director_microdissection.shtml). Director slides utilize an energy transfer coating, bonded to a glass support. Tissue sections (e.g., thin tissue slices) are placed on top of the energy coating, and a UV pulse vaporizes the energy coating to propel cells into the collection tube, allowing precise laser dissection and collection of cells.

In cases in which multiple slides are processed by microdissection, the director slide can be used as a template for processing subsequent slides (e.g., thick slices). For a tissue obtained from a patient, the tissue may be frozen and sliced, such that abnormal cells are distributed throughout multiple slices, relative to particular spatial locations of the tissue. By using a director slide, a technician can ensure that regions targeted in the director slide are also targeted for dissection in subsequent slides (adjacent slices of the tissue), helping to ensure that cells from a particular region of a sample, distributed throughout multiple slides, are collected and processed.

Once properly prepared, the preparations are passed through mass spectrometer 140 to generate one or more of mass spectrum 145. It should be appreciated that each step, stage, or state along the workflow 100 path could also be observed via one or more sensors (e.g., digital cameras, microscopes, probes, mass spectrometer, etc.) to generate intrinsic properties or features of the corresponding state of the samples. Thus, even the end result of the path, mass spectrum 145, is considered an intrinsic property of captured cells 130 as well as an intrinsic property of biological samples 120D.

After microdissection, following the second path, the digitally observed state of biological samples 120C can include interesting intrinsic properties. As an example, consider the holes left behind after microdissection in samples 120D. Each hole can be digitally characterized to create digital features representing the state corresponding to biological samples (after processing, e.g., dissection) 120D. As in the previous stages, the digital features derived from biological samples 120C (e.g., shape descriptors, hole shapes, hole arrangements, etc.) can be used to index information about the specimen or identify the specimen. These features can also be used to link back to the previous states.

Finally, in the example shown, a final state is achieved in workflow 100. In this case the final version of the samples are stored in a storage facility 150. The storage location information can also be linked back to the previous states thereby forming a whole life cycle sample tracking chain or blockchain audit trail. One should further appreciate that additional stages beyond storage can also exist and can be tied to the previous states of the sample tracking chain. For example, a person might retrieve the sample from storage facility 150 in order to conduct further review. If so, one or more aspects of the event (e.g., retrieval of the sample, user who retrieved the sample, date of retrieval of the sample, length of time the sample was removed from storage, etc.) can be recorded and logged within the sample tracking chain described below along with the current intrinsic properties of the sample at the point of time.

Although the environment associated with workflow 100 is presented from the perspective of a biological sample being prepared for microdissection, it should be appreciated that the core features of tracking samples via their intrinsic properties can all be applied to other types of samples beyond tumor samples. Thus, the inventive subject matter is considered to cover tracking other types of samples including saliva, urine, blood, ovum, sperm, stool, skin, sweat, or other types of biological samples. It is also specifically contemplated that the inventive techniques can be applied to other types of organisms beyond humans including mammals in general, wildlife, protozoa, fungi, plants, or other organisms. Still further, the techniques can be adapted for use in other arenas beyond sample tracking including managing environmental studies (e.g., geological samples, plot study samples, water samples, soil samples, etc.), supply chain management, clinical trials, research and development projects, gem supply chain tracking, gem cutting, manufacturing, notebook tracking, animal husbandry (e.g., horses, dog breeding, etc.), or arenas where state information can be tracked via the intrinsic properties of objects.

Figure 2:
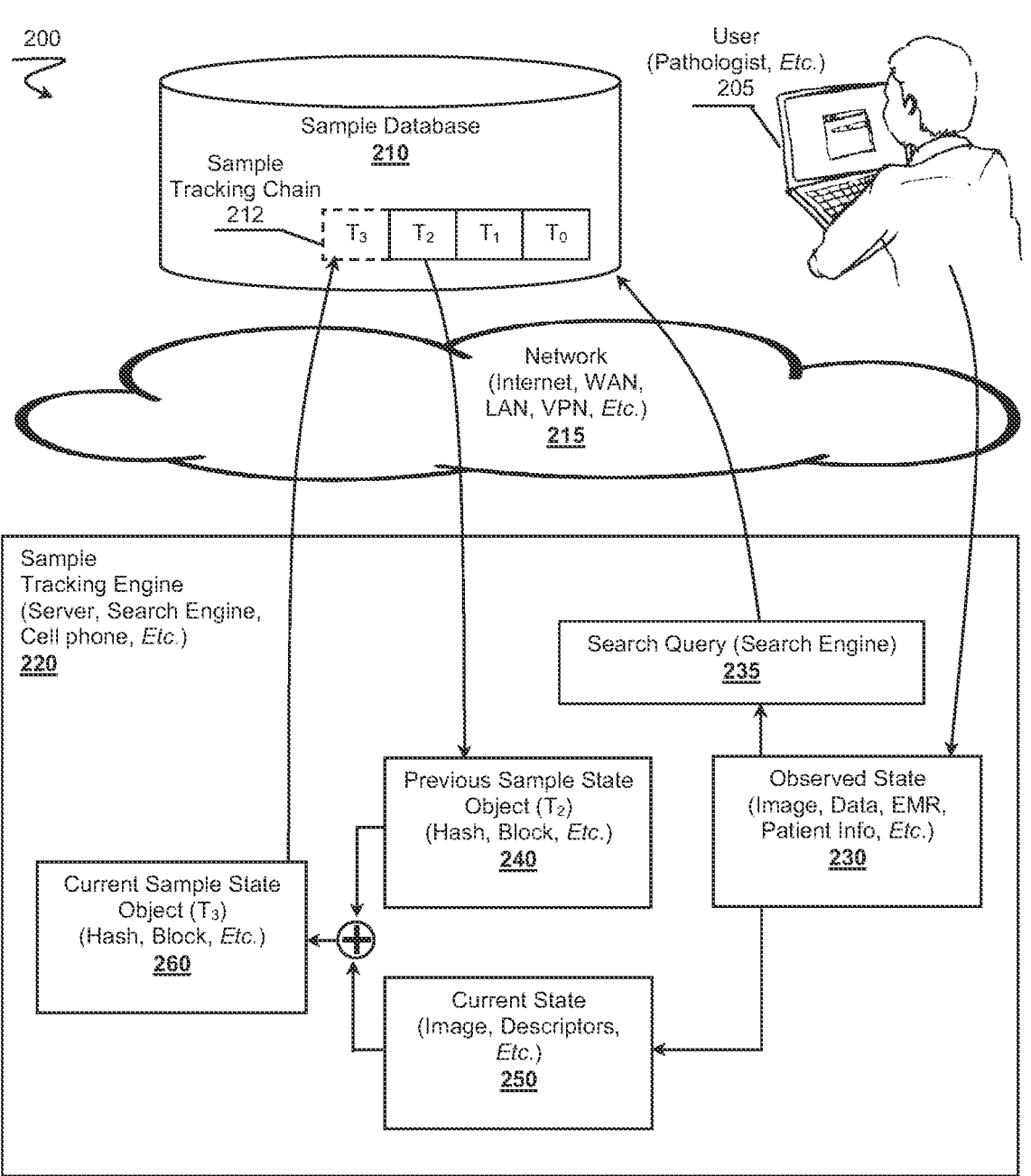
FIG. 2 illustrates an example embodiment of a biological sample tracking system that leverages intrinsic information of a sample, according to an embodiment of the techniques disclosed herein.

FIG. 2 illustrates sample tracking environment 200 where intrinsic properties or features of a biological sample are used to create sample tracking chain 212. Sample database 210 stores one or more of sample tracking chain 212 where each sample tracking chain 212 represents a life cycle or possibly an audit trail of a biological sample. Although one stakeholder is illustrated, user 205, it should be appreciated that the environment can support multiple users or other stakeholders who wish to interact with one or more of sample tracking chain 212.

Sample tracking chain 212 represents one or more digital data records stored on a computer readable non-transitory memory. In the example shown, sample tracking chain 212 is stored in the memory of sample database 210; as records in a file system, on a hard disk, or in RAM for example. Sample database 210 is a computing device configured to retrieve data relating to sample tracking chain 212 based on one or more query criteria that can be defined according to the indexing system of sample database 210. In some embodiments, sample database 210 and/or sample tracking engine 220 can operate as a sample tracking search engine. Example database technologies that are suitable for use in constructing sample database 210 include MySQL, No SQL, MongoDB, Riak, CouchDB, OpenCog, or ArangoDB, just to name a few. In some embodiments, sample database 210 could also include a look-up table in memory or even an entire blockchain that comprises sample tracking chains 212. When sample tracking chain 212 is implemented as a blockchain, sample database 212 could be implemented as a blockchain browser configured to accept queries. Sample tracking chain 212 or its individual state objects are indexed by the corresponding intrinsic properties of the sample's various states.

Sample database 210 is coupled with sample tracking engine 220 to allow sample tracking engine 220 to access sample tracking chain 212. In some embodiments, as shown, sample tracking engine 220 communicatively couples with sample database 210 over network 215 (e.g., Internet, intranet, WAN, LAN, WLAN, P2P, wireless, cellular, ad-hoc, etc.). Network 215 can include a wireless network (e.g., WUSB, 802.11, 802.15, 802.16, cellular, etc.), wired network (e.g., Ethernet, circuit switched network, ATM, etc.), or combination of wireless and wired networks.

Sample tracking engine 220 comprises a computing device configured to track biological samples via their intrinsic properties or features. In some embodiments, sample tracking engine 220 comprises a server system that provides access to its services via a web interface (e.g., HTTP, HTTPS, TCP/IP, UDP/IP, etc.). In other embodiments, sample tracking engine 220 can also include a workstation or even a mobile device that is capable of accessing sample database 210 either local to sample tracking engine 220 (e.g., in the same computer, on the same network) or remote to sample tracking engine 220 (e.g., over the Internet, WAN, etc.). Yet in other embodiments, sample tracking engine 220 can operate as a cloud-based infrastructure (e.g., IaaS, PaaS, SaaS, Chain-as-a-Service, etc.) possibly based on one or more existing cloud systems (e.g., Amazon AWS, Microsoft Azure, Google Cloud, etc.).

Sample tracking engine 220 has numerous roles and responsibilities within environment 200 with respect to aiding user 205 to track, store, or access information related to a biological sample. User 205, a pathologist for example, works with a biological sample whose state information is stored (or will be stored) as sample tracking chain 212. User 205 provides sample tracking engine 220 sample data in the form of an observed state 230. For example, observed state 230 could include a digital image of a tissue on a slide or could include microdissection masks information for a tumor tissue. It should be appreciated that observed state 230 comprises digital data received from or generated by user 205 via a computing device operated by user 205. In the case of observed state 230 comprising image data, for example, observed state 230 could include a digital image of at least a portion of a sample slide at 40× magnification or other magnification. Although digital image data is discussed in detail within this disclosure, it is also contemplated that observed state 230 could include other modalities of data depending on the nature of the sample. Example modalities include audio data, spoken utterance data, biometric data, kinesthetic data, tactile data, olfactory data, taste data, sensor data, texture data, or other data modalism within the human senses or beyond the human sense.

Sample tracking engine 220 leverages observed state 230 multiple ways to proceed with tracking a sample. Following a first path, sample tracking engine 220 obtains access to one or more of sample tracking chain 212 from sample database 210 where sample tracking chain 212 is related to a target biological sample of interest. Sample tracking engine 220 compiles one or more pieces of information related to the sample of interest from observed state 230. In some embodiments, observed state 230 can include one or more pieces of data that represent a patient identifier or a sample identity/identifier as well intrinsic data about the physical sample. Sample tracking engine 220 leverages the compiled information (e.g., patient ID, sample ID, intrinsic properties, etc.) to construct search query 235 targeting the indexing system of sample database 210 operating as a search engine for example. For example, the query could include an SQL query that includes the patient's social security number and/or their name as well as derived features from observed state 230.

Search query 235 can take on many different forms depending on the implementation of sample database 210 or sample tracking engine 220. In some embodiments, search query 235 could be less structured and represent a set of attribute-based values derived from observed state 230 or keywords. The values of the attributes can then be submitted to sample database 210, which in turn returns a results set of sample tracking chains 212 or portions of sample tracking chains 212 that have similar attributes satisfying search query 235. In more interesting embodiments, search query 235 includes search criteria that can include required features or include optional features. Sample database 210 can return the results set ranked according to how well each result satisfies the query possibly based on one or more similarity measures, calculated based on derived intrinsic properties of the physical sample. For example, a similarity measure could include calculating a difference in circularity between two tissue boundaries of tissues mounted on slides or could be a "distance" between intrinsic features such as derived descriptors.

In the example shown, sample tracking engine 220 retrieves at least one previous sample state object 240 from sample database 210 based on search query 230. Previous sample state object 240 is an instantiated data object, which represents at least one previously recorded state of the target biological sample. In this example, the target biological sample is illustrated as having three older states listed as $T_0$, $T_1$, and $T_2$ that represent three snap shots in time. Although sample database 210 returns $T_2$ as previous sample state object 240, it should be appreciated that sample database 210 could also return a NULL value indicating that no record yet exists, return a portion of a matching sample tracking change 212, or even return complete sample tracking chain 212. Previous sample state object 240 is not necessarily required to be an immediately preceding state. However, in most straightforward embodiments, previous sample state object 240 is an immediately preceding state relative to the data observed in observed state 230.

Previous sample state object 240 can be packaged through various techniques. In some embodiments, previous sample state object 240 can be presented to sample tracking engine 220 in its native form; e.g., as a binary record, a file, raw text, or other format by which previous sample state object 240 is stored. In other embodiments, sample database 210 can re-package previous sample state object 240 into a desired format for delivery to sample tracking engine 220. Example formats can include a CSV file, a binary object, a BLOB, a serialized data structure (e.g., YAML, XML, JSON, etc.), or other formats. Of particular interest, previous sample state object 240 can include a block token, typically a hash digest, which represents or identifies previous sample state object 240. In some aspects, a hash digest is a bit string of a fixed size, e.g., about 128 to 256 bits in length, or more. A hash function may be used to map data of an arbitrary size to a fixed size hash digest. If one bit of the arbitrary data changes, a different digest will be generated by the hash function. Therefore, hash digests are suitable for tracking data integrity as well as other applications as presented herein. In other aspects, a cryptographic function may be used to generate the hash digest (e.g., SHA-256, RIPEMD, scrypt, etc.). Block tokens are discussed in more detail below.

Sample tracking engine 220 also generates or otherwise instantiates one or more of current state 250 representative of observed state 230 of the target biological sample of interest. Current state 250 can be an intermediary data structure stored in the memory of sample tracking engine 220 in preparation of creating a new state object. For example, current state 250 can include copies of data from observed state 230 including digital images, video, audio, or other forms of data. It is also possible that current state 250 could just be observed state 230. However, in some embodiments, current state 250 also includes the salient parameters or features derived from observed state 230 as well as other data compiled in preparation for creating a new state object. Example salient parameters can include one or more digital signatures (e.g., descriptors, features, etc.) generated or derived from the digital data of observed state 230. With respect to digital images, current state 250 could include one or more descriptors generated according to one or more image processing algorithms. The descriptors could include one or more of the following types of descriptors SIFT, SURF, GLOH, TILT, DAISY, HOG, uncanny edges, corners, blob descriptors, textures, shape descriptors, or other types of descriptors. In some embodiments, the descriptors could include descriptors of a global vocabulary similar to those described in U.S. patent application publication no. 2015/0262036 to Bing et al. titled "Global Visual Vocabulary, Systems and Methods", filed on Feb. 13, 2015. One advantage of using a global vocabulary is that the descriptors are more compact (i.e., more efficient to transfer) and are more deterministic relative to raw descriptors. It should be appreciated that such descriptors represent values representative of the intrinsic features of the target biological sample as they are generated based on a direct observation of the sample. Still further, current state 250 can include extrinsic data as desired including bar code information, RFID codes, patient or donor identifiers, sample identifiers, identifier of user 205, time stamps, metadata, location, or other types of information.

Once the data associated with current state 250 has been collected, sample tracking engine 220 instantiates current sample state object 260 in memory as a function of current state 250 and previous sample state object 230. When current sample state object 260 is instantiated, it can be initially created having NULL values that are then populated after instantiation. Alternatively, current sample state object 260 can be created having fully fleshed out values by passing data from current state 250 and previous sample state object 240 to the constructor method of current sample state object 260. In some embodiments, current sample state object 260 can also be constructed based on external data. More specifically, the external data can include a hash digest from one or more external distributed, public ledgers (e.g., BitCoin, LiteCoin, Ethereum, etc.). In some cases, a timestamp associated with sample tracking environment 200 may become corrupt or inaccurate. According to certain aspects, external data from a public ledger, e.g., a hash digest associated with BitCoin, can be used as a notary, providing an independent measure of the validity of the timestamp associated with the sample state object. The public ledger data or hash digest acts as an external timestamp that is independent of the sample tracking chain with respect to a particular point of time or a time thereafter. Thus, generating a current sample state object using the public ledger provides an independent validation that the data from the corresponding block has not been tampered with or modified.

One should note that the block of data represented by current sample state object 260 depends intimately on the previous state of the target biological sample. Thus, a blockchain of intrinsic states are formed. Still further current sample state object 260 can include one or more types of sample metadata possibly including time data, date data, procedure data, diagnosis data, stakeholder data, care provider data, image data, geo-location data, address data, sample data, insurance data, workstation data, workflow data, or other types of metadata related to the sample.

Sample tracking engine 220 links current sample state object 260 to previous sample state object 230 to continue building the sample tracking chain. For example, current sample state object 260, labeled as $T_3$ to show it is the next state in time, could include the data from current state 250 as well as a hash digest generated by hashing data from current state 250 along with a hash digest from the previous sample state object 240. The linking function used to combine or otherwise link the previous sample state object 240 with the current state 250 is shown by the "Circled-Plus" symbol. Once current sample state object 260 has been instantiated and linked, sample tracking engine 220 updates sample tracking chain 212 in sample database 210 with the newly created and link current sample state object 260. Sample tracking chain 212 can be updated by sample tracking engine 220 sending current sample state object 260, possibly in a serialized format (e.g., XML, YAML, JSON, etc.), to sample database 210 over network 215. Further, sample tracking chain 212 and current sample state object 260 can be indexed by the newly generated intrinsic properties or features derived from observed state 230.

The approach of building a chain of states to form sample tracking chain 212 can be considered as building a blockchain similar to those typically used in many cryptocurrencies; BitCoin for example. However, there are notable differences. Cryptocurrencies create a single blockchain representing the entirety of all transactions ever conducted, which creates an ever growing and unwieldy data structure. Further, cryptocurrencies typically require peer computing devices, referred to as miners, to provide proof-of-work or proof-of-stake in order to combine blocks into the blockchain, which can incur significant time before a block is added to the chain, not to mention significant computing resources. The disclosed approach does not have such disadvantages. Rather, sample tracking chain 212 can be instantiated as a single stand-alone chain for a single sample and represent the sample's life cycle or even represent the sample's audit trail. Thus, sample tracking chain 212 can remain self-contained and small without incurring unlimited growth. Further, sample tracking chain 212 does not require a significant amount of work to create a next block, rather sample tracking engine 220 can quickly execute the desired linking function without requiring a solution to a time consuming cryptographic puzzle (e.g., proof of work, a hash digest with a specific signature, etc.). Still, it should be appreciated that the sample tracking chain 212 could compose a larger more comprehensive blockchain of many samples or even be integrated into other blockchains (e.g., Ethereum, etc.) once privacy concerns are addressed.

Additionally, according to other aspects, another distinction between the present techniques and other blockchain approaches is that the sample tracking chain is updated based on a workflow of a sample. In some aspects, a workflow comprises multiple processing steps, with one or more steps in the workflow altering the physical appearance of the sample (e.g., from staining, dissection, purification, crystallization, suspension or dissolution in another solution, adding one or more reagents to cause a chemical reaction, etc.). Thus, the sample tracking chain provides a way in which to track the biological sample through the entire workflow, maintaining a record of appearance and morphology changes at various steps of the workflow. In some approaches, each step of the workflow may be recorded in the sample tracking chain. In other approaches, a subset of steps of the workflow (e.g., the steps associated with a change in a physical appearance, a change in location, etc.) are recorded in the sample tracking chain. Thus, these techniques are suitable for managing a population of patient samples, at different processing stages of a workflow, to reduce errors occurring from sample mix-ups. This technique is distinct from other types of transaction based distributed ledgers, which simply record changes in the ledger arising from a transaction event (and not from processing steps). Having stated these advantages, it is also specifically contemplated that sample tracking chain 212 could be built within a private (or public) distributed blockchain ledger system.

Sample tracking chain 212, and its individual blocks, can be indexed through many techniques, which provides for quick retrieval or management. In view that sample tracking chain 212 comprises many states where each state has its own intrinsic properties, the values or metrics derived from the intrinsic properties of each state can then be used to index sample tracking chain 212 in addition to the corresponding portions of the sample tracking chain 212. Thus, when the physical sample is analyzed or observed, one or more metrics associated with the physical sample's intrinsic properties can be used to retrieve corresponding portions of sample tracking chain 212 or portions (e.g., blocks, etc.) within sample tracking chain 212. Still further, sample tracking chain 212 can be indexed based on extrinsic information about the corresponding physical sample. Example extrinsic information includes patient data, insurance data, healthcare provider data, stakeholder data (e.g., identification information related to user 205, etc.), timestamps, study or research product data, metadata, or other information that extends beyond the intrinsic properties derived from the physical sample.

For the sake of discussion, consider a scenario where user 205 is a pathologist working with tissue mounted slides created from a patient's tumor. The pathologist is tasked with identifying regions of interest within each slide to determine which regions are likely to contain cancerous cells. The pathologist has several options to recall information associated with the biological sample. In more pedantic scenarios, the slide under observation is tagged or encoded with extrinsic information relating to the sample and/or patient; bar codes for example. In more interesting scenarios, the pathologist scans the slide via a digital microscope to create a digital slide image. As the pathologist begins his task, the digital slide image can be sent to sample tracking engine 215 as observed state 230. Sample tracking engine 220 executes one or more implementations of an image processing algorithm on the digital image to create one or more features, typically referred to as descriptors. Example features can include edge descriptors, image descriptors (e.g., SIFT, TILT, DAISY, etc.), texture descriptors, shape descriptors, or other types of digital features. One should appreciate that such descriptors are generated directly from the physical sample and are therefore considered to represent the intrinsic nature of the physical sample. The features can then be combined into search query 235, which is submitted to sample database 210. In response, sample database 210 retrieves sample tracking chain 212 that has been previously indexed according to such features and/or descriptors. At this point, sample tracking engine 220 has retrieved sample tracking chain 212, or at least a portion of sample tracking chain 212 as represented by previous sample state object 240. It should be appreciated that the intrinsic properties of the sample under consideration are used to retrieve the sample's historical data. Such an approach does not exclude using extrinsic information (e.g., bar codes, QR codes, labels, RFID, etc.) to retrieve information. However, the disclosed approach is considered superior to exclusive use of extrinsic information because the intrinsic properties ensure that accessing sample information is internally consistent, which reduces potential errors generated by mishandling or mislabeling of samples. Example techniques for storing and retrieving information based on image descriptors are described in U.S. Pat. No. 7,016,532 to Boncyk et al. titled "Image Capture and Identification System and Process", filed Nov. 5, 2001; U.S. Pat. No. 7,680,324 to Boncyk et al. titled "Use of Image-Derived Information as Search Criteria for Internet and Other Search Engines", filed Aug. 15, 2005; U.S. Pat. No. 7,565,008 to Boncyk et al. titled "Data Capture and Identification System and Process" filed Jan. 26, 2006; and U.S. Pat. No. 7,899,252 to Boncyk et al. titled "Object Information Derived from Object Images" filed Sep. 28, 2009.

Figure 5:
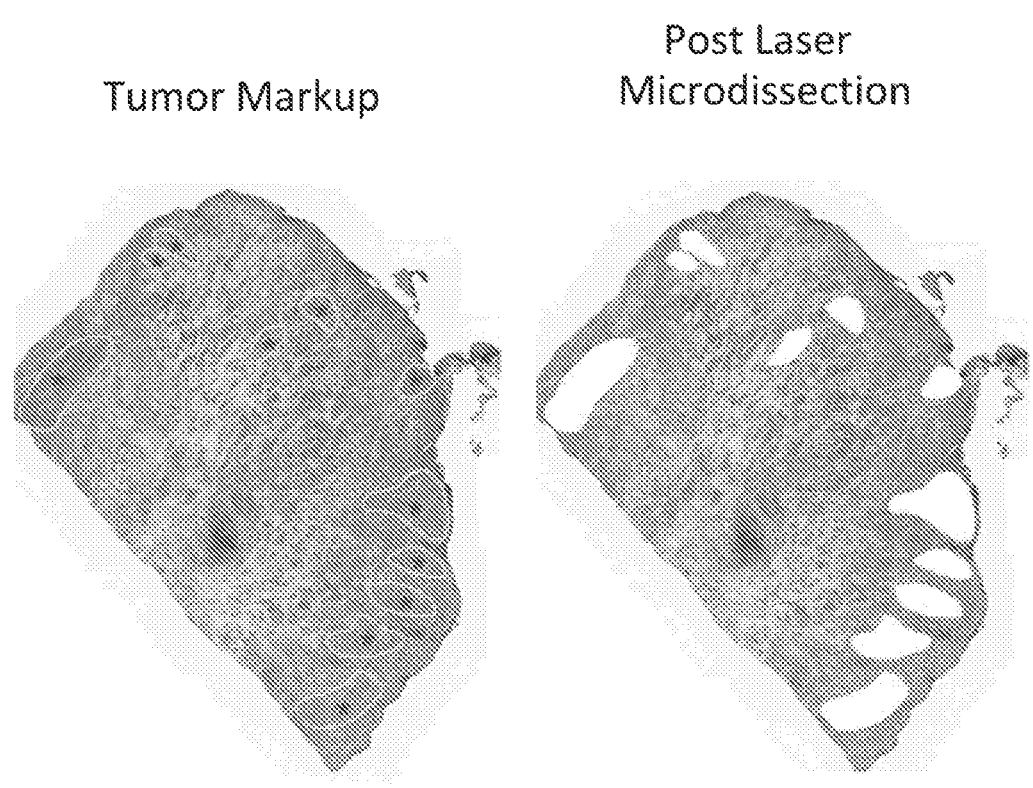
FIG. 5 presents a real-world example image of a tumor tissue specimen prepared on a slide before and after micro-dissection, according to an embodiment of the techniques disclosed herein.

Continuing with this example, the pathologist identifies regions of interest by creating one or more microdissection masks or tumor markups that represent areas of the tissue that should be removed via LCM for further analysis. There are several points of note here. First, the regions of interest can be analyzed with respect to intrinsic features found in those regions. For example, if a region is to be microdissected, then the corresponding intrinsic features from the regions used to index sample tracking chain 212 will also be removed from the specimens. However, once the regions of interest are removed from the tissue such intrinsic features will no longer be present in the physical sample. Thus, these "removed" intrinsic features can be tagged with metadata in sample database 210 to indicate that they are optional indexing features rather than required indexing features when retrieving sample tracking chain 212 or corresponding sample state object (240 or 260). Second, the shapes of the regions of interest (e.g., the masks) can be quantized via one or more shape descriptors according to one or more implementations of shape analysis algorithms. The shape descriptors can be considered to represent the intrinsic shapes of the sites for microdissection (see FIG. 5 showing a slide having a tissue specimen with microdissection masks (left) and holes after microdissection (right)). The mask shape descriptors can be included in current state 250 and can be used to validate that the sample is processed properly after microdissection by comparing the pre-dissection shape descriptors with the actual post-dissection shape descriptors. If the actual post-dissection shape descriptors satisfy matching criteria relative to the pre-dissection shape descriptors, then the microdissection task can be considered as validated. Example shape descriptors that can be used include those generated by one or more implementations of shape algorithms including centroid invariance to bound point distributions, distribution of perpendicular distance to a boundary from axis of least inertia, distribution of average bending energy, measure of eccentricity (e.g. principal axes method, minimum boundary rectangle method, etc.), circularity ratios, ellipse variances, rectangularity, convexity, solidity, Euler number, profiles, hole area ratio, centroid distant distribution, tangent angle distributions, tangent space distributions, contour curvature distributions, area distributions, triangle area distributions, chord length distributions, square or polar shape matrices, shape context, or other types of shape descriptors (Park, UCI iCAMP 2011 "Shape Descriptor/Feature Extraction Techniques").

Although FIGS. 1 and 2 provide an example workflow of a biological sample undergoing staining, dissection, and mass spectrometry, the techniques presented herein are not limited to this example workflow. In general, the techniques presented herein can be used to track any number of samples through one or more steps of a workflow. For example, companies providing genetic analysis services could utilize the sample tracking techniques provided herein, to monitor each sample as it is processed (e.g., through various stages of DNA sequencing workflows, RNA sequencing workflows, proteomics analysis workflows, immunoassay workflows, biomarker analysis workflows, purification workflows, or any combination thereof, etc.), to greatly reduce errors arising from manual handling of samples. Additionally, if processing errors or discrepancies are discovered at a later point in time (e.g., from mishandling by a particular technician, from contamination introduced by a particular instrument, from using a defective reagent in an assay, etc.), these techniques can be used to precisely identify which samples of a population of samples have been affected, rather than presuming the entire population has been affected. The techniques presented herein could also be applied to hospitals or other medical facilities, to track processing of instrumentation used in surgical procedures, especially instrumentation that is reused during surgery or diagnostic screening. As an example, if a particular surgical instrument, used in multiple surgical procedures, is discovered to have not been properly decontaminated between surgeries, the population of patients contacted with the particular surgical instrument could readily be identified, instead of all patients undergoing surgical procedures at a particular facility.

Other examples for which the techniques presented herein apply include tracking art work. Intrinsic properties of a piece of art (e.g., statues, paintings, diamonds, etc.) can be tracked and combined with the sale or display of (at a museum) the piece of art. Intrinsic properties include, e.g., weight; size; for paintings: type of frame, media type; for sculptures; material/media type; for gems: clarity, brilliance; etc. of the piece of art.

Still other examples for which the techniques presented herein apply include land or other infrastructure surveys. Changing properties of a piece of land (e.g., images and other measurements to track changing dimensions due to an updated survey, a sale of the land or a portion thereof, appropriation for commercial use, addition of a public thoroughfare, rezoning, landscaping, structures associated with the land, buildings at various states of construction, property damage, etc.) or of infrastructure (e.g., images and other measurements to track degradation, damage, repair or construction of bridges, roadways, including the use of topography descriptors (such as LIDAR) to document the same) can be tracked as a function of time.

Other examples include manufacturing workflows, including automotive assembly, semiconductor fabrication, gem cutting, large and small scale pharmaceutical and biologic manufacturing, as well as other types of manufacturing processes, etc. Intrinsic properties of a manufacturing process can be tracked as a function of time including automotive processes (by tracking components, order of component assembly, technician, time to assembly, etc.); semiconductor fabrication processes (e.g., wafer size, wafer shape, doping chemicals, lithography/fabrication steps, batch number, post-fabrication verification and testing, technician, etc.); large and small scale pharmaceutical and biologic manufacturing processes (e.g., reagents, time of addition of reagents, technician, impurities, formation of product, viral or bacterial contamination, formation of side products, etc.).

Still other examples for which the techniques presented herein apply include tracking biological samples for prolonged periods of time (e.g., cord blood which may need to be available to a patient over a lifetime), tracking environmental samples that may be transported from various locations to a central storage facility, for tracking biological samples or evidence obtained at a crime scene and subject to later forensic analysis, for tracking the extent to which a disease, such as the flu or Ebola, has spread to particular locations as part of epidemiology studies.

Figure 3:
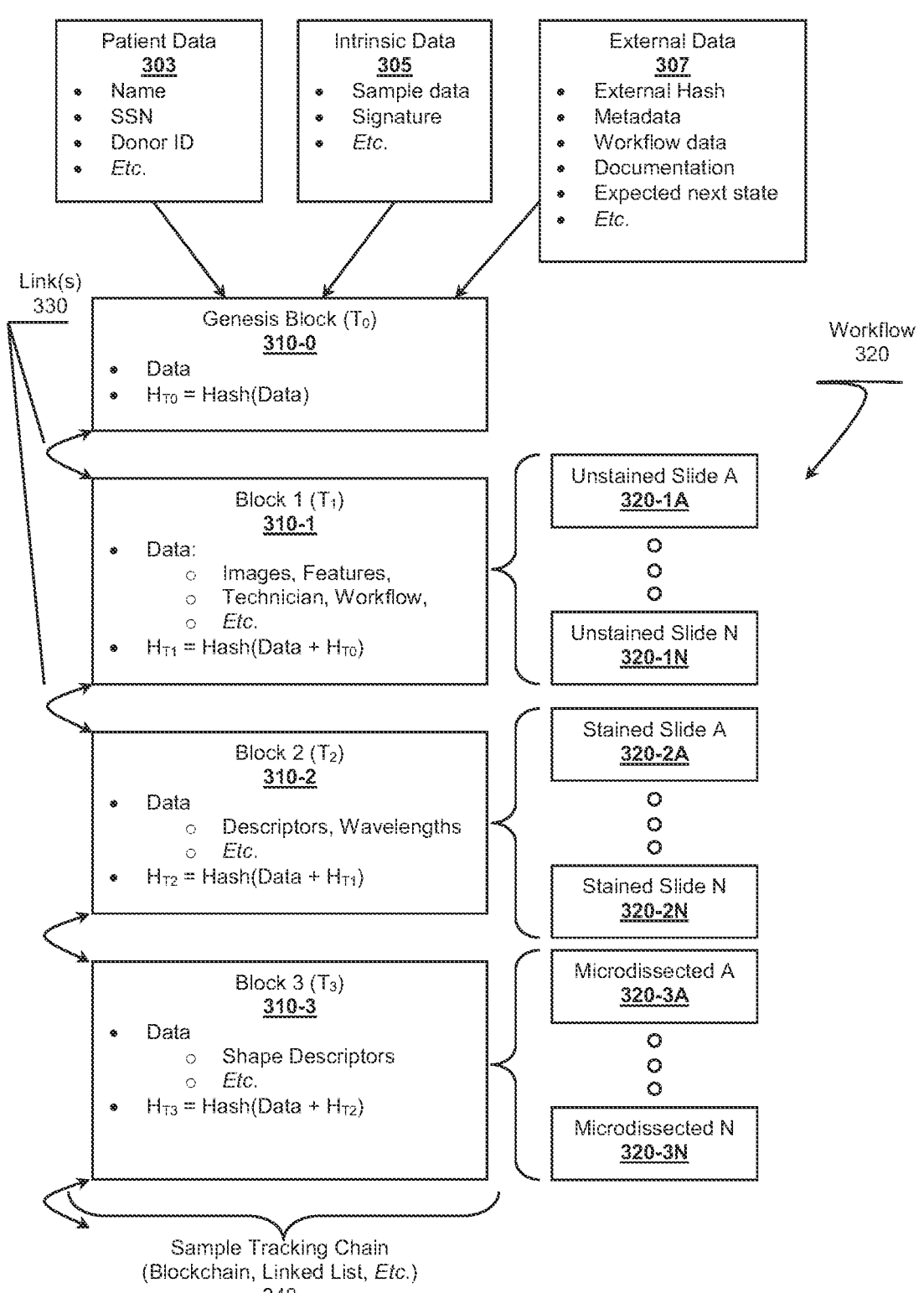
FIG. 3 presents an example schematic of a sample tracking chain as a data structure where the chain comprises blocks of intrinsic sample state information, according to an embodiment of the techniques disclosed herein.

FIG. 3 illustrates example details of a sample tracking chain as represented by sample tracking chain 340. Sample tracking chain 340 represents a chain of sample state data structures where each portion of the data structure links to a next portion. Further, each state comprises digital data that includes information regarding the intrinsic state of a corresponding biological sample. In the example shown, sample tracking chain 340 comprises a blockchain where each portion of the chain is a block of data represented by blocks 310-0 through 310-3, collectively referred to as blocks 310, coupled with neighboring blocks. Each of blocks 310 includes intrinsic sample data derived from an observed state of the physical sample. It should be appreciated that the term "blockchain" is used herein in a similar fashion as used with respect to cryptocurrencies (e.g., Bit-Coin, LiteCoin, PeerCoin, etc.). Sample tracking chain 340 represents the life cycle of one or more biological samples as chronicled by the sample's states via the intrinsic properties of the samples.

In other embodiments, a sample state object may be used to validate a subsequent sample state object. As an example, in histopathology, regions of interest are drawn onto a particular sample side (e.g., at block 310-2), and therefore, the shape of the sample after dissection can be predicted (e.g., at block 310-3). Thus, the sample tracking chain techniques presented herein can provide a way of predicting what a sample will look like after a processing step and can identify discrepancies (e.g., arising from sample mix-ups or processing mistakes). For example, if the sample after dissection does not correlate with the prediction to within a specified threshold, an alert can be sent to a technician. In some embodiments, a director slide can be used to predict the shape of samples after dissection.

To increase the integrity of the sample tracking chain, various approaches can be implemented to help ensure that each block being added to a sample tracking chain is correct. For example, the information in subsequent blocks of the blockchain can be correlated with earlier blocks, e.g., for steps in a defined ordered workflow, such as staining followed by microdissection, or using descriptors or other metadata associated with a particular step of the process, such as a particular computer, a particular location, a particular technician, a corresponding work schedule of the technician, a physician order for a particular type of analysis, etc. As an example, assume a physician orders a biomarker blood test for patient A and a biopsy within staining and tissue analysis for patient B. Assuming that only technician A performs biomarker analysis at Lab N on Instrument A, and only technician B performs staining and dissection of tissue at Lab N using Instrument B, then the system can correlate the physician's order with the processing of each sample by patient name to detect anomalies in the blockchain data. Thus, sample state objects or blocks that would be flagged for review include: patient A, technician A, and instrument B; or patient B, technician A, and instrument B.

In still other aspects, a technician or an automated program can classify cell type regions of interest (e.g., fat versus normal versus tumor) associated with a particular slide. The intrinsic properties of the slide, as captured by the sample tracking chain, can be used to improve data validity, helping to avoid sample mix-ups and to ensure that a respective slide is associated with the proper corresponding patient. It should be appreciated that the disclosed techniques of establishing validated data provides an excellent source for machine learning. As sample tracking chains accumulate, the information in the chains can be compiled into machine learning training data sets, which can then be used to train implementations of machine learning algorithms. For example, sample tracking chains that have identified regions of cancer cells in slides can be identified quickly to create a neural network trained to identify cancer cells in new slides. Stakeholders will have a higher degree of confidence in the training data set because the slide chains have been essentially validated.

For the sake of discussion sample tracking chain 340 begins existence upon the creation of a biological sample, a tumor sample for example. Initially, sample tracking chain 340 can be instantiated as a NULL object via a constructor API call where the features of sample tracking chain 340 can be populated via one or more subsequence API calls. For example, sample tracking chain 340 can be instantiated through creation of genesis block 310-0. Genesis block 310-0 comprises a data structure associated with the creation of the biological sample including patient data 303, external data 307, or intrinsic data 305. Patient data 303 includes various digital information associated with the patient or other donor of the biological sample. Example patient data includes name, social security number, address, insurance information, care giver (e.g., doctor name, etc.), or other information associated with the patient. In some embodiments, patient data 303 can also include one or more public and/or private patient keys that allow a patient to authorize access to one or more portions of sample tracking chain 340. It should be appreciated that sample tracking chain 340 can be indexed via one or more fields within patient data 303 so that stakeholders can leverage known patient information to retrieve sample tracking chain 340 or its blocks as desired.

External data 307 represents optional data that can be included in genesis block 310-0 where external data 307 is beyond the intrinsic nature of the target biological sample or related to the patient. For example, external data 307 could include metadata representing time stamps, workflow information, procedure codes (e.g., CPT codes), proposed diagnosis codes (e.g., ICD codes), or other information. More interestingly, one specifically contemplated external data includes an external hash digest that can be used as a validation token for the sample tracking chain 340. The external hash value can be obtained from publicly available distributed ledgers (i.e., public blockchains), possibly from one or more cryptocurrencies. In some embodiments, the external hash value could be the hash digest of the most current validated block of a BitCoin blockchain or Ethereum blockchain. The external hash value becomes a validated timestamp that indicates that genesis block 310-0 could only have been instantiated after the time by which the external hash value was generated. This approach is considered advantageous because it effectively links sample tracking chain 340 to verifiable external sources.

Although external data 307 is illustrated as contributing to genesis block 310-0, it should be appreciated that external data 307 can also be added to each subsequent block in sample tracking chain 340. For example, external data 307 can also include workflow documentation, workflow data (e.g., process codes, technician identifiers, etc.), expected next state, or other information related to the processing of the samples.

Intrinsic data 305 represents a digital representation of the intrinsic properties of the target biological sample. Examples of intrinsic data 305 includes type(s) of sample, mass, size, shape, density, descriptors, digital signatures, or other features related to the sample. In more interesting embodiments, intrinsic data 305 could include invariant intrinsic property data about the sample; intrinsic properties that do not change as the target sample is processed. Genomic sequences (e.g., whole genome sequence, whole exome sequences, known mutations, SNP patterns, RNA-seq data, proteomics, etc.), for example, would be one type of an invariant intrinsic property. Still further, sample tracking chain 340 can be stored and indexed within the database by one or more of the attributes within intrinsic data 305.

Genesis block 310-0 is instantiated at a time equal to zero state ($T_0$; t=0) for the target sample. Genesis block 310-0 includes relevant data obtained from the various source of data (e.g., patient data 303, intrinsic data 305, external data 307, etc.), which can be retrieved assuming proper authentication or authorization is obtained. Further, genesis block 310-0 also includes a block token (see $H_{T0}$) that is generated as a function of data included in the block and that can be used to identify the block. In the example illustrated, the block token is a hash digest ($H_{T0}$) generated according to an implementation of a hash algorithm and as a function of the input data. One should note that this approach can (but is not required to) be used to generate a hash digest that depends on external data 307, including an external hash digest, thereby yielding several benefits. First, an external stakeholder can verify that the data within genesis block 310-0 is valid by re-calculating H from the available data. Second, if the data in genesis block 310-0 is altered, then the stakeholder would be able to detect the change because a re-calculated hash would differ from that value stored in genesis block 310-0. Third, the stakeholder can validate that the data in genesis block 310-0 existed at a time frame corresponding to when the external hash existed as validated by external, public sources.

In some embodiments, genesis block 310-0 may be formed using static data. Some data associated with a patient may be static over a period of time, e.g., social security number, birthdate, location at which the patient sample is obtained. Other data may be variable, such as patient name, level of biomarkers, prognosis, etc. Thus, in some embodiments, the hash digest of the genesis block may be formed using static data, and stored for subsequent comparison to a hash digest of the same static data, in order to verify the integrity of the genesis block. In other examples, data may be stored in the database as attribute value pairs, in order to indicate that a data field has changed. Thus, in some embodiments, static data may be selected as input to a hash function, while in other embodiments, both static data and variable data may be selected as input to a hash function.

Although there are numerous possible algorithms by which the block token can be generated, a few examples of hash algorithms are included here for reference. Example hashing functions include MD5, SHA (e.g., SHA-1, SHA-2, SHA-3, SHA-256, SHA-512, etc.), Whirlpool, BLAKE2, scrypt, or other hashing functions. In general, more secure hash functions are more desirable so that sample tracking chain 340 is more robust against tampering. Thus, a SHA-based hash is more desirable than MD5 because MD5 has been broken. Still further, more desirable hash functions generating larger digests (i.e., the hash value) are more interesting to reduce possible collisions. Therefore SHA-512 can be considered more desirable than SHA-256. In some embodiments, it is desirable to have a hash function that takes longer to generate the digest so that it is computationally difficult to break. In such embodiments, scrypt might be more desirable the SHA-512.

Other types of functions that can be used to generate the block token includes UUID generation functions (e.g., RFC 4122, etc.), GUID generation functions, or other types of identifier generation functions. In more interesting embodiments the block token is generated to be as unique as possible while also depending on the data included in the block and possibly based on external data (e.g., external hash digest, etc.). An example heterogeneous block token could include a string having a GUID plus a hash digest derived from the block data as well as the GUID. Still further, it is contemplated that non-hash-based functions can be leveraged while still respecting the desired traits.

Returning to the example presented in FIG. 3, the reader's attention is directed to workflow 320. Workflow 320 represents a portion of an overarching workflow focused on generating microdissection sites on tissue slides generated from the target biological sample. Although workflow 320 represents a portion of an overarching workflow, the disclosed techniques can be used equally well with more complex workflows having numerous steps or tasks. Workflow 320 starts with the target biological sample being disposed on one or more slides as represented by unstained slides 320-1A through 320-1N, collectively referred to as slides 320-1, where each of these slides includes a cross section of target sample. It should be appreciated that the collection of slides 320-1 can be considered to represent a three dimensional structure of the sample. Thus, one intrinsic property of the sample at this stage could include an inferred 3D model or shape. Therefore, various blocks can be generated from one or more sample state objects from 2D images as well as 3D models of the target biological sample.

In the example shown, unstained slides 320-1 collectively represent a new state of the biological sample. The new state is then used to create a new block, block 310-1, within sample tracking chain 340. In this case, the intrinsic properties of the tissue on slides 320-1, individually or collectively, can be used as a foundation of block 310-1 including actual digital images of the slide (e.g., whole slide image, tissue image, etc.) as the intrinsic data. Further, other intrinsic properties can also be compiled including boundary of the tissue (e.g., edges, boundary, etc.), shape, size, features, or other aspects of the tissue. Similar to block 310-0, block 310-1 can also incorporate external data possibly including workflow metadata (e.g., technician identifier, workflow identifier, workflow task, audit trail information, IEC 62304 compliance data, time stamps, etc.), or even another external hash digest as a validity time stamp as discussed previously (e.g., BitCoin current block hash, LiteCoin current block hash, public ledger hash, etc.). Once the data associated with the new state, state $T_1$ in the example, is compiled, the block 310-1 can be linked to the previous state via one or more of link 330.

In some embodiments, each block 310 can be stored as an individual record in a data store or database. In such cases, link 330 can comprise a data member of block 310-1 that has a value corresponding to the identifier of block 310-0. In other embodiments, blocks 310-0 and 310-1 form a linked list, possibly a double linked list where each block points to the other. Still, in more interesting embodiments, link 330 essentially comprises a linked hash digest forming a blockchain as discussed above where a current sample state object "links" back to a previous sample state object via a hash digest generated based the previous states block token (e.g., hash digest, etc.) and the current states data. In other words, block 310-1 can include a block token (i.e., $H_{T1}$) having the form of a hash digest generated by hashing the data of block 310-1 along with the hash digest of block 310-0 (i.e., $H_{T0}$) where the block token is essentially link 330. In some embodiments, both a hash-based block token and pointers to neighbor blocks are employed.

Block 310-1 is illustrated as having a compilation of all the data from unstained slides 320-1A through 320-1N. However, it is also contemplated that each slide could have its own corresponding block within sample tracking chain 340. In which case, sample tracking chain 340 could have a chain of many smaller blocks. Still in other embodiments, the information from the slides could be arranged into a tree structure where each branch in the tree represents the states of a single slide and the root of the tree represents block 310-1. In such scenarios sample blockchain 340 could be arranged as a Merkle tree to ease generating hash digests from multiple smaller blocks and for low latency access. Thus, the subject matter described herein is considered to include other arrangements of the data beyond a linear chain, including binary trees, AVL trees, side chains, or other data structures.

Workflow 320 continues by transforming unstained slides 320-1 into stained slides 320-2A to 320-2N, collectively referred to as stained slides 320-2. In this example, there is a one to one correspondence between unstained slides 320-1 to stained slides 320-2. However, it is contemplated that in some embodiments such a one-to-one correspondence is not required. For example, in some embodiments one physical specimen could be divided into multiple groups of subspecimens, where each group is processed differently. Stained slides 320-2 can each be stained using the same staining technique or stained using different techniques. As an example, stained slide 320-2A could be stained with hematoxylin while another stained slide 320-2B could be stained with PAS diastase. In such cases, corresponding block 310-2 can include stain identification information for the slides. Each of stained slides 320-2A through 320-2N can be digitized, preferably according to standardized processes, to create a digital images of the slides; whole slide images stored in SVS format (i.e., OpenSlide format; see URL openslide.org/formats/aperio/) for example. Other formats can include Hamamatsu format, Leica format, MIRAX format, Philips format, Sakura format, Trestle format, Ventana format, generic tiled format, or others types of virtual slide formats. Such digital images represent the intrinsic nature of the sample on the slides and can become part of block 310-2.

Still further, in some embodiments stained slides 320-2A through 320-2N can be created by applying multiplex fluorescent immunohistochemistry (IHC) enabled characterization to each slide, possibly leveraging one or more imaging systems as offered by PerkinElmer& (e.g., Vectra® imaging system, Nuance® FX multiplex biomarker imaging system, etc.) or by Optra Systems™ (e.g., OptraScan® automated scanning and high resolution scanning system). Once imaged, the virtual slides can be created from the stained slides based on the light spectrum generated from the slides. Therefore, each of stained slides 320-2A through 320-2N can spawn multiple virtual slides where each corresponding virtual slide extenuates desired intrinsic features of the corresponding sample. Each of the slide images or data files from the IHC characterization can include light spectrum information such as observed wavelengths of light (e.g., 350 nm to 900 nm, etc.). Interestingly, each "spectrum" view of the slides can be digitally analyzed according to different algorithms as desired to generate one or more additional intrinsic features (e.g., descriptors, metrics, etc.). Still further, each region of a slide can be analyzed differently based on the collective intrinsic features that appear in the regions. For example, a region having a high nuclear density could be analyzed differently than a region have a high edge descriptor density. Example techniques for recognizing or classifying specific regions of an image using different techniques based on density are described in U.S. patent application publication 2015/0161474 to Jaber et al. titled "Feature Density Object Classification, Systems and Methods", filed Dec. 9, 2014.

The digitized slides images can then be compiled (e.g., files, raw data, BLOBs, markup language files, etc.) for incorporation into the next block, block 310-2 in the example, of sample tracking chain 340. Still, in some embodiments, the digital slide images are not required to be part of the block. In such cases, block 310-2 can include pointers to where the slide images are stored. The pointers can include digital object identifiers (DOIs), URLs, URIs, slide identifiers (e.g., GUIDs, UUIDs, etc.), or other types of address through which the slides can be accessed. Such an approach is considered advantageous in scenarios that leverage public, distributed ledgers while also requiring to keep the actual data private.

In addition to the digitized images of stained slides 320-2, block 310-2 can also include additional information that aids in identifying the sample at this stage of the workflow. Each digitized image can be processed by one or more implementations of image processing algorithms to derive identifying features (e.g., descriptors, textures, wavelengths, densities, metrics, etc.) As discussed previously, the identifying features can include image descriptors (e.g., SIFT, HOG, edge descriptors, TILT, etc.). SIFT is described more fully in U.S. Pat. No. 6,711,293 to Lowe titled "Method and Apparatus for Identifying Scale Invariant Features in an Image and Use of Same for Locating an Object in an Image", filed Mar. 6, 2000. Example edge descriptors are described in U.S. Pat. No. 9,412,176 to Song et al. titled "Image-Based Feature Detection using Edge Vectors" filed May 6, 2015. The resulting descriptors generated by the algorithms can also be compiled into block 320-2 and also used to index sample tracking chain 340 and/or block 320-2 for later retrieval. Interestingly, the approach of incorporating such descriptors into sample tracking chain 340 provides for using image-based object recognition techniques to retrieve block 320-2 without requiring that the actual image data, which might be private, to be present.

Once the data is compiled for the newly generated stained state, block 310-2 can be finalized by creating its block token. Again, similar to block 310-1, the block token of block 310-2 is illustrated as a hash digest of the new state's compiled data along with the hash digest from the previous state's block 310-1; $H_{T1}$ in this case. The new hash digest, H-r, essentially represents link 330 back to block 310-1. Some embodiments of block 320-2 can also include other forms of link 330 (e.g., GUIDs, UUIDs, URLs, record identifiers, etc.) in block 310-2.

For the sake of brevity, example workflow 320 skips one or more steps that might appear in a typical workflow in order to focus on microdissected slides 320-3A through 320-3N, collectively referred to as microdissected slides 320-3, which are of particular interest. Microdissected slides 320-3 represent a state of the target biological sample after the slides have been microdissected, possibly via LCM, leaving one or more holes in the tissue sample on the slide. As a reference, the reader's attention is directed to FIG. 5, which shows an example slide image. The left image shows a tissue sample showing a tumor markup indicating where microdissection should occur. The markup illustrates multiple microdissection masks generated by a pathologist. The right image shows the same exact tissue sample post microdissection, which corresponds to one of microdissected slides 320-3. Note that the post microdissected tissue represents yet another new state of the target biological sample where the tissue sample now comprises multiple holes of various shapes. The holes are new intrinsic features for the sample and each hole can be digitally characterized. As discussed previously, the holes can be characterized by one or more shape descriptors, where the shape descriptors can also be used to index the new sample state and/or sample tracking chain 340. One should also appreciate that the microdissection slides 320-3 can be validated against the tumor markups or masks generated during a previous stage in workflow 320. Note the similarity of the mask shapes on the left side image of FIG. 5 relative to the actual microdissection holes of the right side image. The before and after shape descriptors for each region (i.e., mask versus corresponding hole) can be compared individually as well as collectively. In some embodiments, if the before and after shape descriptors are sufficiently similar to or within a threshold or other similarity criteria, then the post-microdissection slide is considered a valid state relative to the pre-microdissection slide. The similarity measure could be based on a Euclidean distance between the two shape descriptors depending on the nature of the shape descriptor.

Other forms of validation can also be employed. In embodiments where each block includes expected next state data (i.e., external data), the sample tracking engine processing sample tracking chain 340 can compare the expected next state in a previous sample state object to the current state. If there is agreement between the expected next state and the current state, then the current state can be considered as comprising a valid state. One example was presented previously with respect to microdissection masks. Another example can include a scenario where block 310-1 associated with unstained slides 320-1 could include expected stain information (e.g., spectral information, expected colors, etc.). When stained slides 320-2 are observed, the observed colors or spectral information (e.g., multiplex IHC, etc.) can be measured and compared to the expected stain information. If the two match to within matching criteria, the stained slides 320-2 can be considered valid. Thus, inventive subject matter is considered to include the concept of real-time validation of workflow states as a function of sample tracking chains 340.

Beyond characterizing the holes in microdissected slides 320-3, the arrangement of the holes in the slides can be characterized. Metaphorically, the holes in the slide can be considered an intrinsic bar code for the slide. Thus, once a slide is imaged, the holes can be digitally analyzed generating one or more whole slide descriptors which can then be used to identify or index the slide. One possible descriptor could include a histogram that represents the area of each hole relative to the area subtended by the entire tissue. The bins of the histogram can be arranged by relative distance from the centroid of the tissue to the outer most edge. The radial distance from the tissue centroid to the centroid of the hole can determine into which bin the hole or holes falls. The number of bins in the histogram can be any practical number; 5, 10, 15, or more bins for example. Such a descriptor is rotationally invariant and image resolution invariant. Thus a user is not required to take identical images of the slide to reproduce a similar descriptor.

As with the previous blocks and sample states, the image data and/or hole descriptors can be compiled into a data set for incorporation into block 310-3 representing a new state of the target tissue. Continuing from the perspective of building a blockchain, block 310-3 also has a block token representing the state in the form of a hash digest (i.e., $H_{T3}$) generated as a function of the block's data (e.g., one or more of images of microdissected slides, hole shape descriptors, hole arrangement descriptors, etc.) as well as the previous state's block token (i.e., the hash digest from block 310-2; $H_{T2}$). Again, the new hash digest $H_{T3}$ becomes link 330 back to block 310-2.

Sample tracking chain 340 as presented only has four shown blocks representing four states for illustrative purposes and is not considered limiting. Rather, it should be apparent to the reader that sample tracking chain 340 can include any arbitrarily large number of blocks and/or corresponding states. Such chains can include thousands, millions, or even more blocks depending on the nature of the chain.

Sample tracking chain 340 is also illustrated as a single, standalone chain. In some embodiments, sample tracking chain 340 can compose larger structures having many other features. For example, sample tracking chain 340 can take the form of a side chain that links to or branches from a patient's healthcare blockchain. In other similar scenarios, sample tracking chain 340 can be a part of the patient's healthcare blockchain. Example healthcare blockchains that can leverage the disclosed approach are described in U.S. patent application publication 2015/0332283 to Witchey titled "Healthcare Transaction Validation via Blockchain Proof-of-Work, Systems and Methods", filed May 13, 2015.

Sample tracking chain 340 is not limited to being part of a patient or sample specific structure, but can also be part of a larger collection of data. More specifically, sample tracking chain 340 can be part of a larger clinical study chain comprising blocks of data associated with the progress of the study. Each block of the clinical study chain can be constructed to chronical the progress of the study as well as archive each patient's healthcare data, including the patient's personal tracking chain 340 that might be a side chain relative to the study's blockchain. The advantages of such an approach are clear. Providing such "study tracking chains" ensures that once data is collected, it cannot be altered without significant difficulty because the entire chain would have to be re-built in order to introduce false data. Therefore, the study data is more robust against falsification after the study is complete. In some embodiments, using public, as opposed to private, distributed blockchain, falsification of the data is even more difficult because such falsification would not stand against public external scrutiny. According to the techniques herein, computation of each block can be performed in a time efficient manner, minimizing lag time between computing states of the sample chain.

There are numerous techniques available by which sample tracking chain 340 can be instantiated. In simple embodiments, sample tracking chain 340 comprises a set of data blocks linked by recursive hash digests, possibly along with pointers. Each block could be stored as a separate record in a database. However, more interesting embodiments provide for instantiation of sample tracking chain 340 as a true blockchain where the blockchain can be part of a private ledger or part of a distributed public ledger. Existing technologies that can be adapted for use to create sample tracking chain 340 include BitCoin, Ethereum (see URL www.ethereum.org), or the Hyper Ledger Project (see URL www.hyperledger.org) just to name a few.

In view that the blocks of the blockchain can include patient information, the data can be secured via one or more cryptographic techniques (e.g., 3DES, AES, ECC, etc.). For example, the private data stored in the blocks of sample tracking chain 340 can be encrypted based on a patient's private key. Upon authorization from the patient, or other authorized agent, a stakeholder can be permitted to access the data based on patient's key possibly using existing key exchange techniques. Further, access to private data within sample tracking chain 340 can occur via establishing one or more secure sessions within a homomorphic environment as discussed in U.S. patent application publication U.S. 2016/0105402 to Soon-Shiong et al. titled "Homomorphic Encryption in a Healthcare Network Environment, Systems and Methods", filed Jul. 21, 2015.

Interestingly, sample tracking chain 340 can store data as discussed above or can be externally referenced as a document. For example, sample tracking chain 340 can be referenced via a URL where the domain of the URL references the sample tracking chain 340 and/or blocks (e.g., www.<sample chain domain name>.com/<block ID>/<data member ID>/, etc.). Sample tracking chain 340 can also be referenced by or point to DOIs. Yet further, sample tracking chain 340 can be referenced by or point to health object identifiers (HOI) associated with a patient. HOIs are discussed in more detail in U.S. patent application publication 2014/0114675 to Soon-Shiong titled "Healthcare Management Objects", filed Jan. 3, 2014.

In some embodiments, sample tracking chain 340 can be stored within a graph database. Each state or block in sample tracking chain 340 can be stored as a node within the graph database schema where the transition from one state to another represents the edge between the nodes. Further, extrinsic information can be stored as properties for the nodes and/or edges. Thus, the graph database can be used to retrieve quickly relevant information not just about individual sample tracking chains 340, but relevant information from collections of sample tracking chains 340 having similar graphs with similar properties. Such an approach is advantageous when storing or analyzing R&D studies or clinical trial studies where the system stores sample tracking information across numerous patients or for large cohorts. Example graph database implementation that can be leveraged to store sample tracking chain 340 include Neo4j, OpenCog, and ArangoDB among others. In some embodiments, graph databases such as OpenCog, which provides an AI framework, might be more desirable when sample tracking chains 340 are coupled to treatments and outcomes of patients. Such a coupling provides a solid foundation for generating automated, reasoned hypotheses about a new patient's possible outcomes based on comparison of the patient's sample tracking chain 340 to previous, known sample tracking chains and outcomes. Example reasoning engines that can be adapted to leverage graph database implementations of sample tracking chain 340 are described in U.S. Pat. No. 9,262,719 to Soon-Shiong titled "Reasoning Engines", filed internationally on Mar. 22, 2012.

One should appreciate that sample tracking chain 340 also provides a solid foundation for compliance with one or more regulations. For example, sample tracking chain 340 can include block-level data that complies with IEC 62304 audit trail requirements, 21 CFR part 11 requirements, HIPPA regulations, HL7 support, or other features.

FIG. 4 presents example computer implemented method 400 of managing or creating a digital sample tracking chain. The steps of method 400 can be executed by one or more processors according to software instructions stored in a non-transitory computer readable memory. Example computing devices that can be configured to operate as a sample tracking engine or search engine according to method 400 include medical imaging devices (e.g., slide scanners, etc.), cell phones, web servers, work stations, tablet computers, cloud-based servers, or other computing devices having access to sample intrinsic state information.

Method 400 begins with step 410, which includes generating a genesis block of a sample tracking chain. The genesis block as discussed above is a block of digital data that includes a representation of intrinsic properties or features of a target biological sample. Additionally, the intrinsic properties represent the initial state of the target biological sample typically just after extraction from a source. Example intrinsic properties can include sample mass, sample shape, number of samples, tissue type, dielectric properties, mechanical properties, acoustic properties, density, elasticity, or other properties relating to the sample. The genesis block can also include data associated with the donor or source of the biological sample (e.g., social security number, name, donor identifier, etc.). In typical embodiments, the donor is a human patient; however, the donor could also be other types of animals or living organisms. Example donor data can include a sample donor identifier such as a sample location, procedure codes (e.g., CPT codes, etc.), diagnosis codes (e.g., ICD codes, etc.), a patient name, a patient identifier, a slide identifier, a genome sequence, an address, an insurance identifier or other donor information. The genesis block can also include external or extrinsic data from other sources possibly including bar codes, RFID codes, labels, workflow identifiers, task identifiers, audit trail codes, or other information. One specific type of external data that is contemplated for inclusion in the genesis block includes a hash value or digest obtained from a block of an apriori existing external distributed public ledger (e.g., BitCoin, Ethereum, HyperLedger, etc.). The external hash digest provides an authoritative and verifiable marker or token indicating that the sample was taken after a specific point in time. Once the data associated with the genesis block of the sample tracking chain is compiled, the collected data (e.g., donor data, intrinsic sample data, external data, etc.) is used to generate a block token that substantially identifies the genesis block. In more preferred embodiments, the block token comprises a hash digest of the block's data where the hash digest is generated according to one or more implementations of a hash algorithm. Once the genesis block is instantiated, it can be stored in a database or other storage system indexed by the intrinsic properties of the sample or other attributes (e.g., patient name, sample ID, etc.). It is also contemplated that the genesis block can be stored within a public or private distributed ledger. The genesis block becomes the initial block of the sample's corresponding sample tracking chain that chronical the life of the sample. Such a chronical is also considered to provide an audit trail for the sample. In some embodiments, the genesis block can be constructed from static data, e.g., social security number, birthdate, etc. The hash digest may be stored locally, for comparison to a regenerated hash digest using the same data at a later point in time. In this example, both hash values should be identical, and therefore, can be used to verify the integrity of the genesis block.

Step 420 focuses on providing access to the sample tracking chain once it is in existence. Thus step 420 can serve as a basis for a device operating as a search engine or as a basis for a device operating as a sample tracking engine that updates the sample tracking chain with new sample state information based on observed intrinsic sample properties or features. Step 420 includes a device (e.g., sample tracking engine, sample search engine, etc.) obtaining access to the sample tracking chain of a target biological sample. One or more intrinsic properties are derived from a digital representation of the target biological sample. In some scenarios, the digital representation includes raw sensor data (e.g., image sensor data, probe data, etc.). In other scenarios, the digital representation could include audio data, image data, video data, or other data modalities captured in real-time or from a digital recording. The intrinsic properties, possibly in conjunction with other data related to the sample, can be compiled into a query (e.g., SQL command, keywords, look-up indices, etc.), which can then be submitted to the sample database storing one or more of the sample tracking chains. In more preferred embodiments, the query is constructed according to the namespace or schema by which the sample tracking changes are indexed in the database. For example, one or more image descriptors derived from a digital image of the sample can be submitted as a query to the sample database. The database returns a results set of having zero (i.e., no match or a NULL match) or more sample tracking chains that satisfy the query. Returning to the example of using image descriptors, the sample database can return one or more sample tracking changes having similar image descriptors. If more than one sample tracking chain is returned, they can be ranked by how well their image descriptors match the query image descriptors. The ranking could be based on a variant of term frequency (e.g., descriptors) and inverse document frequency (TF-IDF). In view that the query can be constructed based on intrinsic properties of the sample as well as other data (e.g., donor name, sample ID, extrinsic data etc.), errors in extrinsic data entry or sample labels are mitigated. In previous approaches to archiving sample information, the indices used to index the sample information relied solely on extrinsic information. Such extrinsic information is heavily subject to human error possibly due to incorrect data entry, mislabeling, or other factors. Thus, the disclosed approach reduces false positives by also relying on actual intrinsic features of the sample, providing an improvement over error-prone manual processes.

Step 430 includes retrieving a previous sample state object from the sample tracking chain. The previous sample state object includes at least one portion of the sample tracking chain that has data representing a previous state of the target biological sample. If the sample tracking chain is being created de novo based on a newly observed state, then the previous sample state object can be considered a NULL object or considered a newly instantiated object that can be fleshed out based on the newly observed state. If the sample tracking chain already exists, then the previous sample state object can be a block of data from a blockchain. The block, as discussed with respect to FIG. 3, can include one or more block tokens that identify the block and is generated as a function of the block's data along with previous state information; a hash digest from a previous block for example. The previous sample state object is used as a foundation for creating a new block. In typical embodiments, the previous sample state object is an immediately preceding block. However, it is also contemplated that the previous sample state object could be any previous state of the target biological sample or could even be a complete blockchain associated with the target biological sample.

Step 440, which can be considered an optional step, includes validating the target biological sample by calculating a similarity measure between a current observed state and at least one of the previous sample state objects in the sample tracking chain. In view that each state object, that is each block in the blockchain, includes digital intrinsic features of the biological sample, it is possible to compare the current state's digital features to those found in previous sample state objects. Consider, as an example, where the previous sample state object represents a whole slide image and includes a number of image descriptors, possibly including edge descriptors generated from the outline or boundary of the tissue on the slide. Note that the edge descriptors can be used to index the previous sample state object as well as the corresponding sample tracking chain. Continuing the example, assume that the current observed state includes a whole slide image of the same slide after microdissection. Although sections of the tissue sample have been removed, thus possibly removing one or more image descriptors, the outline of the tissue in the sample can remain substantially intact. This means that edge descriptors associated with the boundary of tissue largely remains intact. Thus, the edge descriptors can be used for several purposes. First, the edge descriptors of the tissue boundary in the microdissected slide can be used to retrieve the sample tracking chain or previous sample state object, possibly based on a nearest neighbor search (e.g., a k-NN search, approximate NN search, etc.). Second, the boundary edge descriptors of the microdissected tissue of can be compared to the previous edge descriptors before microdissection to generate a similarity measure. The similarity measure can be calculated as a function of the Euclidian distance between pairs of the most similar before and after microdissection edge descriptors. A final similar measure could be just the sum of the Euclidian distances, possibly after normalization; when close to zero, the two tissue sample states are very similar and can be considered a valid match. If the similarity measure has a large positive value, then the states are dissimilar. The threshold value used for such a similar measure will depend on the nature of the descriptors, normalizing the measure, number of descriptors, or other factors. All similarity measures based on sample features are contemplated. Thus, when the two states are found to be similar, the new state can be considered a valid state for the target biological sample under consideration.

Step 450 includes generating a current state representative of an observed state of the target biological sample. The observed state comprises the raw data or data files associated with the one or more sensors (e.g., cameras, probes, etc.) or other data sources and that represent the target biological sample. In some embodiments, the observed state can include a digital image of the target biological sample, for example. The digital image could be an image of the entire sample or images of portions of the sample. In some scenarios the digital image could be a micrograph that captures portions of the sample at various magnifications; 10×, 20×, 40×, and/or more. With respect to slide images of a tissue, a 40× magnifications would likely comprise cell-level details. The current state is instantiated from the observed state. In some embodiments, the current state stores the same data as the observed state. In such cases, the current state and observed state could be the same data structure. Still, in more interesting embodiments, the current state also includes one or more digital features (e.g., image descriptors, edge descriptors, shape descriptors, nucleus density, Voronoi diagrams, etc.) from the observed state data. It should be appreciated that the terms "current state" and "observed state" are used to mean intermediary data objects storing data related to the biological sample in preparation for creating a full block object.

Step 460 focuses on creating a new block object for integration into the sample tracking chain. Step 460 comprises deriving a current sample state object as a function of the current state, as discussed with respect to step 450, and the previous sample state object. The current sample state object represents a fully instantiated block of data that can be integrated within the sample tracking chain. Typically the current sample state object includes the desired sample state data from the current state (e.g., image data, descriptors, audio data, video data, etc.) representing the intrinsic features of the target biological sample. Of particular interest, the current sample state object also includes a block token, a hash digest for example, that is generated from current data as well as a block token from the previous sample state object. For example, as indicated by step 465, generating the block token for the current sample state object can include calculating a hash digest for the current sample state object based on the previous state's hash digest. Such a hash digest can be a concatenation of the previous state's hash and the current state data. Further, the hash digest could include multiple iterations of the same hash function (e.g., SHA-512(SHA-512(data))) or a heterogeneous mix of hash functions (e.g., SHA-512(scrypt(data))) to reduce hash collisions. In some embodiments, the creation of the current sample state object can also include creating the block within a distributed ledger system (e.g., Ethereum, HyperLedger, BitCoin, etc.) by solving a cryptographic puzzle as proof-of-work. In such cases, the block token can include a hash digest having a particular signature (e.g., number of leading zeros, desired bit patterns, etc.). Still further, the current sample state object can incorporate external information, an external public ledger hash digest for example, to validate that the data in the current sample state object was in existence by a certain, well-defined time.

Step 470 includes linking the current sample state object to the previous sample state object in the sample tracking chain. In some embodiments, generating a hash digest from the previous sample state object forms the link as described in step 465. While, in other embodiments, the newly created or instantiated block can include a pointer back to the previous sample state object or the previous sample state object can be updated with a pointer that points to the newly created current sample state object thereby forming a double linked list where each block links to its neighbors.

Step 480 includes updating the sample tracking chain with the current sample state object. Depending on the implementation, this step can take on different characteristics. In a linked list-based system, the current sample state object can be stored in a database and the previous sample state object can be updated with a pointer as discussed in step 470. Still, in other blockchain embodiments, the sample tracking chain is updated to incorporate the block representing current sample state object where the sample tracking chain is a single record. When the sample tracking chain is part of a distributed ledger, the sample tracking chains located on peer devices can receive updates to the sample tracking chain over a network. For example, a sample tracking engine that successfully creates the current sample state object, possibly based on a proof-of-work or other "proof" model, can submit the current sample state object to other peers in the distributed ledger system by packaging the current sample state object as a new block encapsulated in one or more digital formats (e.g., XML, YAML, WSDL, binary objects, etc.) and sent via one or more protocols (e.g., TCP/IP, UDP/IP, HTTP, HTTPS, FTP, etc.).

Additionally, when the ledger is distributed and involves a plurality of computers, consensus techniques known in the art for updating blockchains may be utilized, including proof of work algorithms which ensure that the next link in the blockchain is authentic and has not been tampered with, proof of stake algorithms that rely on validators to create blocks and for other computers to sign off on the block, etc. All such techniques are contemplated for use herein.

Step 485 includes indexing the sample tracking chain in a sample tracking database according to digital sample features derived from a digital representation of the target biological sample. The digital sample features can include global sample features (e.g., whole slide image descriptors, tissue border edge descriptors, etc.), sample state features (e.g., stains, color maps, etc.), or various descriptors (e.g., image descriptors, edge descriptors, shape descriptors, color descriptors, texture descriptors, etc.). The sample tracking chain as well as the current sample state object can be indexed with the intrinsic features derived from the observed state. The intrinsic features can include the image descriptors, edge descriptors, digital signatures, measured features, shape descriptors, metrics, or other features that can be derived or measured from the digital representation of the observed state. As discussed previously, indexing the sample tracking chain and as well as the current sample state objects based on intrinsic features of the sample enables fast and valid retrieval of the data. Although method 400 focuses on building sample tracking information based on the intrinsic properties or features of the target biological sample, it is also contemplated that the sample tracking chain and its state objects (e.g., blocks in the sample tracking blockchain, etc.) can be indexed by extrinsic information as well; bar codes, patient identifier, metadata, etc.

The sample tracking chain can continue to grow according to one or more of the steps described above as desired. The resulting tracking chain has numerous clear technical benefits. First, the life cycle of the target biological sample is chronicled and can be quickly retrieved via a computing device based on the intrinsic features operating as a digital index of the sample at any point in time. Second, the sample data can be validated by external stakeholders via the stakeholders using a computing device re-calculating the various block tokens in the chain. Further, the stakeholders can validate that the data was in existence by certain times based on external hash digests from existing, external public ledgers.

In some embodiments, the sample tracking chain can be a standalone data structure, e.g., an individual data structure. In other embodiments, the sample tracking chain can be part of a larger blockchain infrastructure, e.g., as part of a hyper ledger or other blockchain based infrastructure, or integrated into other existing sample tracking chains or blockchains. In other embodiments, the sample tracking chain can be part of a larger blockchain infrastructure, e.g., associated with a technician or a facility, etc. Examples of storing healthcare data in a large blockchain to create a healthcare historical blockchain (HHBC) may be found in U.S. patent application Ser. No. 14/711,740, which is incorporated by reference herein.

The techniques disclosed herein may also be utilized as an Operating as a Service (OaaS) using an Application Programming Interface (API). Various analytics can be performed on the sample tracking chains, which comprise linked lists of hash digests. Provided that the various sample tracking chains are stored on a suitable infrastructure, hospitals, scientists, companies or other entities desiring access to data in the one or more sample state objects may subscribe to a service to access relevant data. Additionally, the techniques presented herein may be used to store and keep some aspects of data private. For example, by including pointers to imaging slides, a $3^{rd}$ party could be provided with access to the slides, and not confidential patient information associated with the slides.

For example, to review all of the microdissections available for a particular type of lung cancer, or associated with a particular clinical study, one could review the sample tracking chain to identify relevant samples (e.g., only lung microdissection sites). In other examples, sample tracking chains may be reviewed to establish data samples analyzed by a particular data technician or at a particular facility.

To facilitate identification of relevant data, the sample tracking chain can include metadata. Various types of metadata can be collected and incorporated into the sample state object to describe the characteristics of the sample, e.g., 1 mm sample thickness, type of cancer, clinical trial information, etc. The database can be used to store various types of metadata used to characterize the sample and/or to facilitate identification of data of interest, e.g., as part of an OaaS service. It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A computer-based patient sample audit trail system, the system comprising:

at least one non-transitory computer readable memory storing software instructions and a patient sample audit trail comprising a sample tracking chain; and at least one processor coupled with the at least one memory and that executes the following operations upon execution of the software instructions:

obtaining a digital image of at least one assay of at least one patient sample by applying multiplex fluorescent immunohistochemistry (IHC) enabled characterization to at least one slide having the at least one patient sample, and capturing the digital image using an automated scanning system, the at least one assay representing a snap shot in time for a patient;

generating intrinsic properties of the at least one assay from digital descriptors obtained from executing one or more implementations of at least one image processing algorithm on the digital image;

retrieving a previous patient-related state object related to the at least one assay from the sample tracking chain;

instantiating a current state object in the at least one non-transitory computer readable memory as a function of the intrinsic properties and the previous patient-related state object;

updating the sample audit trail in the at least one non-transitory computer readable memory by linking the current state object to the previous patient-related state object in the sample tracking chain; and enabling validation of a target patient sample by comparing intrinsic properties of the target patient sample to intrinsic properties stored in the sample tracking chain, wherein the previous patient-related state object and the current state object comprise an immunoassay workflow.

2. The system of claim 1, wherein the previous patient-related state object represents a previous snap shot in time relative to the snap shot in time.

3. The system of claim 2, wherein the previous snap shot in time is associated with the at least one assay.

4. The system of claim 1, wherein the sample tracking chain comprises a patient-related sample life cycle chain.

5. The system of claim 4, wherein the patient-related sample life cycle chain comprises a whole life cycle chain.

6. The system of claim 1, wherein the sample tracking chain comprises a sample-specific audit trail.

7. The system of claim 1, wherein the sample tracking chain comprises a blockchain-based audit trail.

8. The system of claim 1, wherein the sample tracking chain complies with IEC 62304 audit trail requirements.

9. The system of claim 1, wherein the sample tracking chain complies with 21 CFR part 11 requirements.

10. The system of claim 1, wherein the sample tracking chain comprises HIPPA compliant data related to the at least one patient sample.

11. The system of claim 1, wherein the sample tracking chain comprises a patient's personal tracking chain.

12. The system of claim 11, wherein the patient's personal tracking chain comprises a side chain.

13. The system of claim 1, wherein the sample tracking chain comprises a blockchain.

14. The system of claim 13, wherein the blockchain comprises at least one of the following: a public distributed blockchain ledger, a private blockchain, a semi-private blockchain, and a healthcare historical blockchain.

15. The system of claim 1, wherein the current state object comprises a pointer to external data relative to the sample tracking chain.

16. The system of claim 15, wherein the external data comprises information related to the at least one assay.

17. The system of claim 1, wherein the intrinsic properties relate to a color from the at least one assay.

18. A computer implemented method for processing a patient sample audit trail, the method comprising:

obtaining a digital image of at least one assay of at least one patient sample by applying multiplex fluorescent immunohistochemistry (IHC) enabled characterization to at least one slide having the at least one patient sample, and capturing the digital image using an automated scanning system, the at least one assay representing a snap shot in time for a patient;

generating intrinsic properties of the at least one assay from digital descriptors obtained from executing one or more implementations of at least one image processing algorithm on the digital image;

retrieving a previous patient-related state object related to the at least one assay from a sample tracking chain of a patient sample audit trails stored in at least one non-transitory computer readable memory;

instantiating a current state object in the at least one non-transitory computer readable memory as a function of the intrinsic properties and the previous patient-related state object;

updating the sample audit trail in the at least one non-transitory computer readable memory by linking the current state object to the previous patient-related state object in the sample tracking chain; and enabling validation of a target patient sample by comparing intrinsic properties of the target patient sample to intrinsic properties stored in the sample tracking chain, wherein the previous patient-related state object and the current state object comprise an immunoassay workflow.

19. A computer program product for processing a patient sample audit trail, the computer program product comprising a non-transitory computer readable storage medium having program instructions embodied therewith, the program instructions executable by a processor to cause the processor to:

obtain a digital image of at least one assay of at least one patient sample by applying multiplex fluorescent immunohistochemistry (IHC) enabled characterization to at least one slide having the at least one patient sample, and capturing the digital image using an automated scanning system, the at least one assay representing a snap shot in time for a patient;

generate intrinsic properties of the at least one assay from digital descriptors obtained from executing one or more implementations of at least one image processing algorithm on the digital image;

retrieve a previous patient-related state object related to the at least one assay from a sample tracking chain of a patient sample audit trails stored in at least one non-transitory computer readable memory;

instantiate a current state object in the at least one non-transitory computer readable memory as a function of the intrinsic properties and the previous patient-related state object;

update the sample audit trail in the at least one non-transitory computer readable memory by linking the current state object to the previous patient-related state object in the sample tracking chain; and enable validation of a target patient sample by comparing intrinsic properties of the target patient sample to intrinsic properties stored in the sample tracking chain, wherein the previous patient-related state object and the current state object comprise an immunoassay workflow.

* * * * *